US006544759B1

(12) United States Patent
Harari et al.

(10) Patent No.: US 6,544,759 B1
(45) Date of Patent: Apr. 8, 2003

(54) POLYNUCLEOTIDES ENCODING A NOVEL GROWTH FACTOR WHICH ACTS THROUGH ERBB-4 KINASE RECEPTOR TYROSINE

(75) Inventors: Daniel Harari, Rehovot (IL); Yosef Yarden, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 0 days.

(21) Appl. No.: 09/553,769

(22) Filed: Apr. 21, 2000

(51) Int. Cl.$^7$ ........................... C07K 21/04; C12N 5/00; C12N 15/00; C12N 15/03; C12N 15/06

(52) U.S. Cl. ................... 435/69.1; 435/325; 435/320.1; 536/23.5; 536/23.1; 530/388.22; 530/300; 530/324

(58) Field of Search ............................... 536/23.5, 23.1; 435/320.1, 69.1, 325, 7.1, 35; 530/388.22, 300, 324

(56) References Cited

U.S. PATENT DOCUMENTS 5,350,836 A * 9/1994 Kopchick et al.

FOREIGN PATENT DOCUMENTS

WO     WO 01/14415 A2     3/2001

OTHER PUBLICATIONS

Wells, J.A. (1990) Additivity of mutational effects in proteins. Biochem, 29(37): 8509–8517, esp. Table II.*

Epidermal Growth Factor and Betacellulin Mediate Signal Transduction Through Co–Expressed ErbB2 and ErbB3 Receptors, Maurizio Alimandi, Ling–Mei Wang, Donald Bottaro, Chong–Chou Lee, Angera Kuo, Mark Frankel, Paolo Fedi, Careen Tang, Marc Lippman and Jacalyn H. Pierce, The EMBO Journal, vol. 16, No. 18, pp 5608–5617, 1997.

The Structural Basis for the Specificity of Epidermal Growth Factor and Heregulin Binding, Elsa G. Barbacci, Bradley C. Guarino, Justin G. Stroh, David H. Singleton, Kenneth J. Rosnack, James D. Moyer and Glenn C. Andrews, The Journal of Biological Chemistry, vol. 270, No. 16, Apr. 21, 1995, pp 9585–9589.

New Differentiation Factors: A Family of Alternatively Spliced Neuronal and Mesenchymal Factors, Noa Ben–Baruch and Yosef Yarden, Society for Experimental Biology and Medicine, 1994, pp 221–227.

Neuregulins and Their Receptors: A Versatile Signaling Module in Organogenesis and Oncogenesis, Steve Burden and Yosef Yarden, Neuron, vol. 18, pp 847–855, Jun. 1997.

Neuregulin–2, a New Ligand of ErbB3/ErbB4–receptor Tyrosine Kinases, Kermit L. Carraway III, Janet L. Weber, Michelle J. Unger, Jessica Ledesma, Naichen Yu, Martin Gassmann, & Cary Lai, Nature, vol. 387, May 29, 1997 pp 512–516.

Ligands for ErbB–family receptors encoded by a Neuregulin–like gene, Han Chang, David J. Riese II, Walter Gilbert, David F. Stern, & U.J. McMahan, Nature, vol. 387, May 29, 1997, pp 509–512.

An Immunological Approach Reveals Biological Differences Between the Two NDF/Heregulin Receptors, ErbB–3 and ErbB–4, Xiaomei Chen, Gil Levkowitz, Eldad Tzahar, Devarajan Karunagaran, Sara Lavi, Noa Ben–Baruch, Orith Leitner, Barry J. Ratzkin, Sarah S. Bacus and Yosef Yarden, The Journal of Biological Chemistry, vol. 271, No. 13, Mar. 29, 1996, pp 7620–7629.

The Relationship Between Human Epidermal Growth–Like Factor Receptor Expression and Cellular Transformation in HIH3T3 Cells, Bruce D. Cohen, Peter A. Kiener, Janell M. Green, Linda Foy, H. Perry Fell, and Ke Zhang, The Journal of Biological Chemistry, vol. 271, No. 48, Nov. 29, 1996, pp 30897–30903.

Activation of HER4 by Heparin–Binding EGF–like Growth Factor Stimulates Chemotaxis but not Proliferation, Klaus Elenius, Subroto Paul, Geneve Allison, Jilin Sun and Michael Klagsbrun, The EMBO Journal, vol. 16, No. 6, pp. 1268–1278, 1997.

Aberrant Neural and Cardiac Development in Mice Lacking the ErbB4 Neuregulin Receptor, Martin Gassmann, Franca Casagranda, Donata Orioli, Horst Simon, Cary Lai, Rudiger Klein & Greg Lemke, Nature, vol. 378, Nov. 23, 1995, pp 390–395.

A Heparin–Binding Growth Factor Secreted by Macrophage–Like Cells that is Related to EGF, Shigeki Higashiyama, Judith A. Abraham, Judy Miller, John C. Fiddes, Michael Klagsbrun, Science, vol. 251, pp 936–939.

A Novel Brain–Derived Member of the Epidermal Growth Factor Family that Interacts with ErbB3 and ErbB4, Shigeki Higashiyama, Michiharu Horikawa, Kouji Yamada, Naohiro Ichino, Norihiko Nakano, Takatoshi Nakagawa, Junichiro Miyagawa, Natsuki Matsushita, Toshiharu Nagatsu, Naoyuki Taniguchi and Hiroshi Ishiguro, J. Biochem, vol. 122, No. 3, 1997, pp 675–680.

(List continued on next page.)

Primary Examiner—Elizabeth Kemmerer
Assistant Examiner—Sandra Wegert
(74) Attorney, Agent, or Firm—G.E. Ehrlich Ltd.

(57) ABSTRACT

A novel ErbB-4 ligand, referred to herein as Neuregulin-4 (NRG-4) is disclosed as well as polynucleotide sequences encoding NRG-4, oligonucleotides and oligonucleotide analogs derived from polynucleotide sequences, a display library displaying short peptides derived from NRG-4, antibodies recognizing NRG-4, peptides or peptide analogs derived from NRG-4, and pharmaceutical compositions and methods of employing peptides or peptide analogs, oligonucleotides and oligonucleotide analogs, and/or polynucleotide sequences to up-regulate or down-regulate ErbB-4 receptor activity (signaling).

8 Claims, 10 Drawing Sheets

OTHER PUBLICATIONS

Identification of Heregulin, a Specific Activator of p185$^{erbB2}$, William E. Homes, Mark X. Sliwkowski, Robert W. Akita, William J. Henzel, James Lee, John W. Park, Daniel, Yansura, Nasrin Abadi, Helga Raab, Gail D. Lewis, H. Michael Shepard, Wun–Jing Kuang, William I. Wood, David V. Goeddel, Richard L. Vandlen, Science, vol. 256, May 22, 1992, pp. 1205–1210.

Binding Interaction of the Heregulinβ egfDomain with ErbB3 and ErbB4 Receptors Assessed by Alanine Scanning Mutagenesis, Jennifer T. Jones, Marcus D. Ballinger, Paul I. Pisacane, Julia A. Lofgren, V. Danial Fitzpatrick, Wayne J. Fairbrother, James A. Wells, and Mark X. Sliwkowski, The Journal of Biological Chemistry, vol. 273, No. 19, May 8, 1998, pp 11667–11671.

ErbB–2 is a Common Auxiliary Subunit of NDF and EGF Receptors: Implications for Breast Cancer, Devarajan Karunagaran, Eldad Tzahar, Roger R. Beerli, Xiaomei Chen, Diana Graus–Porta, Barry J. Ratzkin, Rony Seger, Nancy E. Hynes and Yosef Yarden, The EMBO Journal, vol. 15, No. 2, pp 254–264, 1996.

Requirement for Neuregulin Receptor erbB2 in Neural and Cardiac Development, Kuo–Fen Lee, Horst Simon, Hua Chen, Brian Bates, Mien–Chie Hung & Christopher Hauser, Nature, vol. 378, Nov. 23, 1995, pp 394–399.

Synthesis of a Biological Active Tumor Growth Factor from the Predicted DNA Sequence of Shope Fibroma Virus, Yao–Zhong Lin, Gregg Caporaso, Pi–Yin Chang, Xiao–Hong Ke and James P. Tam, Biochemistry, 1988, vol. 27, No. 15, pp 5640–5645.

Glial Growth Factors are Alternatively Spliced erbB2 Ligands Expressed in the Nervous System, Mark A. Marchionni, Andrew D.J. Goodearl, Maio Su Chen, Olivia Bermingham–McDonogh, Cassandra Kirk, Marvin Hendricks, Frank Danehy, Don Misumi, Judith Sudhalter, Kazumi Kobayashi, Diana Wroblewski, Catherine Lynch, Mark Baldassare, Ian Hiles, John B. Davis, J. Justin Hsuan, Nicholas F. Totty, Masayuki Otsu, Robert N. McBurney, Michael D. Waterfield, Paul Stroobant & David Gwynne, Nature, vol. 362, Mar. 25, 1993, pp 312–318.

Rat Transforming Growth Factor Type 1: Structure and Relation to Epidermal Growth Factor, Hans Marquardt, Michael W. Hunkapiller, Leroy E. Hood, George J. Todaro, Science, vol. 223, Mar. 9, 1984, pp 1079–1082.

Multiple Essential Functions of Neuregulin in Development, Dirk Meyer & Carmen Birchmeier, Nature, vol. 378, Nov. 23, 1995, pp 386–390.

Isolation of the Neu/HER–2 Stimulatory Ligand: A 44 kd Glycoprotein That Induces Differentiation of Mammary Tumor Cells, Elior Peles, Sarah S. Bacus, Raymond A. Koski, Hsieng S. Lu, Duanzhi Wen, Steven G. Ogden, Rachel Ben Levy and Yosef Yarden, Cell, vol. 69, Apr. 3, 1992, pp 205–216.

ErbB Tyrosin Kinases and the Two Neuregulin Families Constitue a Ligand–Receptor Network, Ronit Pinkas–Kramarski, Maya Shelly, Bradley C. Guarina, Ling Mei Wang, Ljuba Lyass, Iris Alroy, Mauricio Alamandi, Angera Kuo, James D. Moyer, Sara Lavi, Mirian Eisenstein, Barry J. Ratzkin, Rony Seger, Sarah S. Bacus, Jacalyn H. Pierce, Glenn C. Andrews, and Yosef Yarden, Molecular and Cellular Biology, Oct. 1998, vol. 18, No. 10, pp 6090–6100.

Betacellulin Activates the Epidermal Growth Factor Receptor and erbB–4, and Induces Cellular Response Patterns Distinct from those Stimulated by Epidermal Growth Factor or Neuregulin–β, David J. Riese II, Yamilee Bermingham, Tom M. van Raaij, Sharon Buckley, Gregory D. Plowman, and David F. Stern, Oncogene (1996), 12, pp 345–353.

Severe Neuropathies in Mice with Targeted Mutations in the ErbB3 Receptor, Dieter Riethmacher, Eva Sonnenberg–Riethmacher, Volker Brinkmann, Tomoichiro Yamaai, Gary R. Lewins & Carmen Birchmeier, Nature, vol. 389, Oct. 16, 1997, pp 725–730.

Betacellulin: A Mitogen from Pancreatic β Cell Tumors, Y. Shing, G. Christofori, D. Hanahan, Y. Ono, R. Sasada, K. Igarashi, J. Folkman, Science, vol. 259, Mar. 12, 1993, pp 1604–1608.

A Novel Epidermal Growth Factor with Mitogenic Activity for Rat Primary Hepatocytes, Hitoshi Toyoda, Toshi Komurasaki, Daisuke Uchida, Yasuko Takayama, Toshiaki Isobe, Tuneo Okuyama, and Kazunori Hanada, The Journal of Biological Chemistry, vol. 270, No. 13, Mar. 31, 1995, pp 7495–7500.

The ErbB–2/HER2 Oncogenic Receptor of Adenocarcinomas: From Orphanhood to Multiple Stromal Ligands, Eldad Tzahar, Yosef Yarden, Biochimica et Biophysica Acta 1377 (1998) M25–M37.

Neu Differentiation Factor: A Transmembrane Glycoprotein Containing an EGF Domain and an Immunoglobulin Homology Unit, Duanzhi Wen, Elior Peles, Rod Cupples, Sidney V. Suggs, Sara S. Bacus, Yi Luo, Geraldine Trail, Sylvia Hu, Scott M. Silbiger, Rachel Ben Levy, Raymond A. Koski, Hsieng S. Lu, and Yosef Yarden, Cell, vol. 69, May 1, 1992, pp 559–572.

Neuregulin–3 (NRG3): A Novel Neural Tissue–Enriched Protein That Binds and Activates ErbB4, Dongxiao Zhang, Mark X. Sliwkowski, Melani Mark, Gretchen Frantz, Robert Akita, Yang Sun, Kenneth Hillan, Craig Crowley, Jennifer Brush and Paul J. Godowski, Proc. Natl. Acad. Sci. USA vol. 94, pp. 9562–9567, Sep. 1997.

* cited by examiner

```
  1 AAACGCTGCATGTCTAGCAAAATTTTCTTTTTTTATGGGAATATAAATTTCTGTTGAGGT      (SEQ ID NO:1)
 61 GCTGATTTTCAACCTTAATTCTTCCATCAAGAATGAAACTATTTAAAAATTAAGATGCCA
                                                            M  P    2 (SEQ ID NO:2)

121 ACAGATCACGAGCAGCCCTGTGGTCCCAGGCACAGGTCATTTTGCCTCAATGGGGGATT
     T  D  H  E  Q  P  C  G  P  R  H  R  S  F  C  L  N  G  G  I    22

181 TGTTATGTGATCCCTACTATCCCCAGCCCATTCTGTAGGTGCATTGAAAATTACACCGGA
     C  Y  V  I  P  T  I  P  S  P  F  C  R  C  I  E  N  Y  T  G    42

241 GCACGCTGCGAAGAGGTTTTTCTCCCAAGCTCCAGCATCCCAAGCGAAAGTAATCTGTCG
     A  R  C  E  E  V  F  L  P  S  S  S  I  P  S  E  S  N  L  S    62

301 GCAGCTTTCGTGGTGCTGGCGGTCCTCCTCACTCTTACCATCGCGGCGCTCTGCTTCCTG
     A  A  F  V  V  L  A  V  L  L  T  L  T  I  A  A  L  C  F  L    82

361 TGCAGGAAGGGCCACCTTCAGAGGGCCAGTTCAGTCCAGTGTGAGATCAGCCTGGTAGAG
     C  R  K  G  H  L  Q  R  A  S  S  V  Q  C  E  I  S  L  V  E   102

421 ACAAACAATACCAGAACCCGTCACAGCCACAGAGAACACTGAAGACATACATCCCCAGTG
     T  N  N  T  R  T  R  H  S  H  R  E  H  *                     115

481 AAGGGCATCATTACCTACAAAGGCGGACTGTGGACCATACGACGAGAGAAGCCCATCATC
541 ATGGATGTGTCCCATCATTTCTATGGCAGTCCCAGGATCTCACTCTTCTTGATGCTCTAC
601 TGTTTGATTGTTCATCGTTCACATACAGAAATGACGCTGGTTTCCTGTGTTGACCTTGCA
661 CCCTGCTACTGTCATCACTGGCCTGGAAGTCAGCAGTATAGATAAGGCTGGCCCTGAATT
721 CAAGAGACTCACCTGTTTTTGCCTACTCAGAGTTACTGGAATTAAAGGCATAACAACAAA
781 AAAAAAAAAAAAAAAAAAAGA
```

Fig. 1a

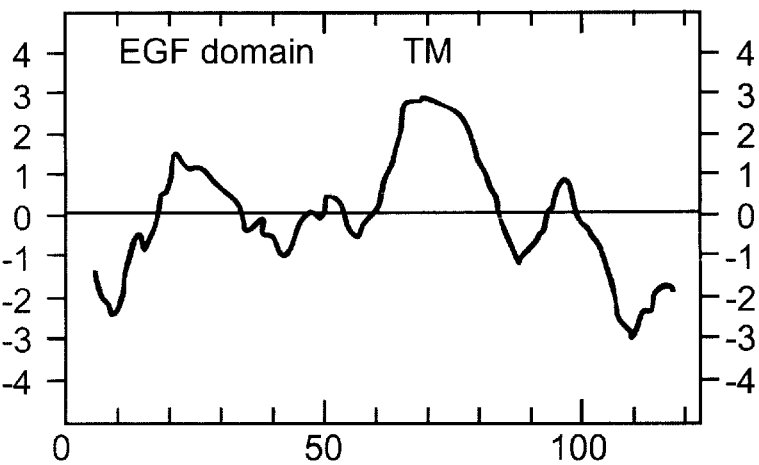

Fig. 1b

| | | A | | B | | C | | SEQ ID NO: |
|---|---|---|---|---|---|---|---|---|
| NRG-4 | DHEQGPRER | SPCNGGICYV | IPSPF... | GRCIENYTGARCEEVEL | | | | 3 |
| NRG-1β | SHLIKCAEKEKTFCVNGGECFLTVKDLSNPSRYLCK | | | CKCPNEFTGDRCQN.YV | | | | 4 |
| NRG-2 | GHARKCNETAKSYCVNGGVCYYIEGINQLS... | | | SKCPVGYTGDRCQQ.FA | | | | 5 |
| NRG-3 | EHFKPCRDKDLAYCLNDGECFVIETLTG.SHKH | | | CRCKEGYQSVECDQ.EL | | | | 6 |
| mouse EGF | NSYPGCPSSYDGYCLNGGVCMHIESLDSYT... | | | CNCVIGYSGDRCQTRDL | | | | 7 |
| human EGF | NSDSECPLSHDGYCLHDGVCMYIEALDKYA... | | | CNCVVGYIGERCQYRDL | | | | 8 |
| TGFα | STCFHFNKCPDSHTQYCFH... | | | GTCRFLVQEEKPA | | | | 9 |
| Betacellulin | THFSRCPKQYKHYCIH... | | | GRCRFVVDEQTPS | | | | 10 |
| Epiregulin | VQITKCSSDMDGYCIH... | | | GQCIYLVDMREKF... | | | | 11 |
| HB-EGF | KKRDPCLRKYKDYCIH... | | | GECRYLQEFRTPS | | | | 12 |
| Amphiregulin | KKKNPCTAKFQNFCIH... | | | GECRYTENLEVT... | | | | 13 |

Fig. 1c

```
mNRG4   22  CCTTAATTCTTCCATCAAGAATGAAACTATTTAAAAATTAAGATGCCAACAGATCACGAG    (SEQ ID NO: 1)
            | || |    |  | |||||||||||||||||||| |||||||||||||||||||||||||
hNRG4    0  TCCTACTCTCTTGACCAAGAATGAAACTATTTACAAATTAAGATGCCAACAGATCACGAA   (SEQ ID NO:14)
mouse                                                                        6   (SEQ ID NO: 2)
human                                                                        6   (SEQ ID NO:15)

mNRG4   82  CAGCCCTGTGGTCCCAGGCACAGGTCATTTTGCCTCAATGGGGGGATTTGTTATGTGATC
            ||||||||||||||||| ||||  ||| ||||||||| |||||||| |||||||||||||
hNRG4   61  GAGCCCTGTGGTCCCAGTCACAAGTCGTTTTGCCTGAATGGGGGCTTTGTTATGTGATA
mouse        Q    G  G  P    R  E  R   S  F  C  L  N  G  G   I   C  L  V  I    26
human        E    C  G  P    S  H  K   S  F  C  L  N  G  G   L   C  L  V  V    26 mNRG4  142  CCTACTATCCCCAGCCCATTCTGTAGGTGCATTGAAAATTACACCGGAGCACGCTGCGAA
            ||||||||  ||||||||| | |||||||| |||||  |||| |  ||||| | ||  |||
hNRG4  121  CCTACTATTCCCAGCCCATTTTGTAGGTGCGTTGAAAACTATACAGGAGCTCGTTGTGAA
mouse        P  T  I   P  S  P  F  C  R  C  L  E  N  Y  T  G  A  R  C          46
human        P  T  I   P  S  P  F  C  R  C  V  E  N  Y  T  G  A  R  C          46 mNRG4  202  GAGGTTTTTCTCCCAAGCTCCAGCATCCCAAGCGAAAGTAATCTGTCGGCAGCTTTCGTG
            ||||||||||||||||| |||||||||||  || ||||||||| || | |||| ||||||
hNRG4  181  GAGGTTTTTCTCCCAGGCTCCAGCATCCAAACTAAAAGTAACCTGTTTGAAGCTTTTGTG
mouse        E  V  F  L  P   S  S  S  I   P   S  E   S  N  L   S  A   A  F  V   66
human        E  V  F  L  P   G  S  S  I   Q   T  K   S  N  L   F  E   A  F  V   66 mNRG4  262  GTGCTGGCGGTCCTCCTCACTCTTACCATCGCGGCGCTCTGCTTCCTGTGCAGGAAGGGC
            |  |||||||||||  |  || ||||  ||  |  ||| ||||||| |||||  ||  ||
hNRG4  241  GCATTGGCGGTCCTAGTAACACTTATCATTGGAGCCTTCTACTTCCTTTGCAGGTGTGGT
mouse        V   A  V  L   L   T   A  A  L  C          K   G             86
human        A   A  V   V   I   G  A  F  Y             C   G             86 mNRG4  322  CACCTTCAGAGGGCCAGTTCAGTCCAGTGTGAGATCAGCCTGGTAGAGACAAACAATACC
             ||      ||    |     |     ||   |     |      || |        | |
hNRG4  301  AACACATGCATGTAGTCCTAGCTGCTTGGGAGGCTGAGATGGGAAGATCGCTTGAGCCCA
mouse        H  L  Q  R  A  S  S  V  Q  C  E  I  S  L  V  E  T  N  N  T       106
human        N  T  C  M  *                                                      90 mNRG4  382  AGAACCCGTCACAGCCACAGAGAACACTGAAGACATACATCCCCAGTGAAGGGCATCATT
            ||| |    |    ||     ||          ||      ||      ||| |
hNRG4  361  GGAATGAGAGGCTGCAGTTAAGCCATGACTGCACTACTGCACTCCTGCCTGGGAAAGGCC
human        R  T  R  H  S  H  R  E  H  *                                     115 mNRG4  442  ACCTACAAAGGCGGACTGTGGACCATACGACGAGAGAAGCCCATCATCATGGATGTGTCC
            || | || ||   || |||    |||    |   |    |       |   ||  |
mNRG4  421  ACTTTCAGAGAGCCAGTTCAGTCCAGTATGATATCAACCTGGTAGAGACGAGCAGTACCA mNRG4  502  CATCATTTCTATGGCAGTCCCAGGATCTCACTCTTCTTGATGCTCTACTGTTTGAT
              |  |   ||  |   | |    |    |     |  |      | |   | |
hNRG4  481  GTGCCCACCACAGTCATGAACAACACTGAAGAAACGTCAAAGTGAACCAAATCATT
```

Fig. 1e

SEQUENCE LISTING

<160> NUMBER OF SEQ ID NOS: 18

<210> SEQ ID NO 1
<211> LENGTH: 750
<212> TYPE: DNA
<213> ORGANISM: Mus musculus

<400> SEQUENCE: 1

| tgttgaggtg | ctgattttca | accttaattc | ttccatcaag | aatgaaacta | tttaaaaatt | 60 |
| aagatgccaa | cagatcacga | gcagccctgt | ggtcccaggc | acaggtcatt | ttgcctcaat | 120 |
| gggggattt | gttatgtgat | ccctactatc | cccagcccat | tctgtaggtg | cattgaaaat | 180 |
| tacaccggag | cacgctgcga | agaggttttt | ctcccaagct | ccagcatccc | aagcgaaagt | 240 |
| aatctgtcgg | cagctttcgt | ggtgctggcg | gtcctcctca | ctcttaccat | cgcggcgctc | 300 |
| tgcttcctgt | gcaggaaggg | ccaccttcag | agggccagtt | cagtccagtg | tgagatcagc | 360 |
| ctggtagaga | caaacaatac | cagaacccgt | cacagccaca | gagaacactg | aagacataca | 420 |
| tccccagtga | agggcatcat | tacctacaaa | ggcggactgt | ggaccatacg | acgagagaag | 480 |
| cccatcatca | tggatgtgtc | ccatcatttc | tatggcagtc | ccaggatctc | actcttcttg | 540 |
| atgctctact | gtttgattgt | tcatcgttca | catacagaaa | tgacgctggt | ttcctgtgtt | 600 |
| gaccttgcac | cctgctactg | tcatcactgg | cctggaagtc | agcagtatag | ataaggctgg | 660 |
| ccctgaattc | aagagactca | cctgtttttg | cctactcaga | gttactggaa | ttaaaggcat | 720 |
| aacaacaaaa | aaaaaaaaaa | aaaaaaaga | | | | 750 |

<210> SEQ ID NO 2
<211> LENGTH: 115
<212> TYPE: PRT
<213> ORGANISM: Mus musculus

<400> SEQUENCE: 2

Met Pro Thr Asp His Glu Gln Pro Cys Gly Pro Arg His Arg Ser Phe
1               5                   10                  15

Cys Leu Asn Gly Gly Ile Cys Tyr Val Ile Pro Thr Ile Pro Ser Pro
            20                  25                  30

Phe Cys Arg Cys Ile Glu Asn Tyr Thr Gly Ala Arg Cys Glu Glu Val
        35                  40                  45

Phe Leu Pro Ser Ser Ser Ile Pro Ser Glu Ser Asn Leu Ser Ala Ala
    50                  55                  60

Phe Val Val Leu Ala Val Leu Leu Thr Leu Thr Ile Ala Ala Leu Cys
65                  70                  75                  80

Phe Leu Cys Arg Lys Gly His Leu Gln Arg Ala Ser Ser Val Gln Cys
                85                  90                  95

Glu Ile Ser Leu Val Glu Thr Asn Asn Thr Arg Thr Arg His Ser His
            100                 105                 110

Arg Glu His
        115

<210> SEQ ID NO 3
<211> LENGTH: 47
<212> TYPE: PRT
<213> ORGANISM: Mus musculus

```
<400> SEQUENCE: 3

Asp His Glu Gln Pro Cys Gly Pro Arg His Arg Ser Phe Cys Leu Asn
1               5                   10                  15

Gly Gly Ile Cys Tyr Val Ile Pro Thr Ile Pro Ser Pro Phe Cys Arg
            20                  25                  30

Cys Ile Glu Asn Tyr Thr Gly Ala Arg Cys Glu Glu Val Phe Leu
            35                  40                  45

<210> SEQ ID NO 4
<211> LENGTH: 49
<212> TYPE: PRT
<213> ORGANISM: Rattus norvegicus

<400> SEQUENCE: 4

Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
            35                  40                  45

Val

<210> SEQ ID NO 5
<211> LENGTH: 46
<212> TYPE: PRT
<213> ORGANISM: Mus musculus

<400> SEQUENCE: 5

Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Val Gly Tyr Thr Gly Asp Arg Cys Gln Gln Phe Ala
            35                  40                  45

<210> SEQ ID NO 6
<211> LENGTH: 48
<212> TYPE: PRT
<213> ORGANISM: Mus musculus

<400> SEQUENCE: 6

Glu His Phe Lys Pro Cys Arg Asp Lys Asp Leu Ala Tyr Cys Leu Asn
1               5                   10                  15

Asp Gly Glu Cys Phe Val Ile Glu Thr Leu Thr Gly Ser His Lys His
            20                  25                  30

Cys Arg Cys Lys Glu Gly Tyr Gln Gly Val Arg Cys Asp Gln Phe Leu
            35                  40                  45

<210> SEQ ID NO 7
<211> LENGTH: 47
<212> TYPE: PRT
<213> ORGANISM: Mus musculus

<400> SEQUENCE: 7

Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30
Cys Val Ile Gly Tyr Ser Gly Asp Arg Cys Gln Thr Arg Asp Leu
            35                  40                  45
```

-continued

<210> SEQ ID NO 8
<211> LENGTH: 47
<212> TYPE: PRT
<213> ORGANISM: Homo sapiens

<400> SEQUENCE: 8

```
Asn Ser Asp Ser Glu Cys Pro Leu Ser His Asp Gly Tyr Cys Leu His
1               5                   10                  15
Asp Gly Val Cys Met Tyr Ile Glu Ala Leu Asp Lys Tyr Ala Cys Asn
            20                  25                  30
Cys Val Val Gly Tyr Ile Gly Glu Arg Cys Gln Tyr Arg Asp Leu
        35                  40                  45
```

<210> SEQ ID NO 9
<211> LENGTH: 46
<212> TYPE: PRT
<213> ORGANISM: Mus musculus

<400> SEQUENCE: 9

```
Ser His Phe Asn Lys Cys Pro Asp Ser Glu Thr Gln Tyr Cys Phe His
1               5                   10                  15
Gly Thr Cys Arg Phe Leu Val Gln Glu Lys Pro Ala Cys Val Cys
            20                  25                  30
His Ser Gly Tyr Val Gly Val Arg Cys Glu His Ala Asp Leu
        35                  40                  45
```

<210> SEQ ID NO 10
<211> LENGTH: 46
<212> TYPE: PRT
<213> ORGANISM: Mus musculus

<400> SEQUENCE: 10

```
Thr His Phe Ser Arg Cys Pro Lys Gln Tyr Lys His Tyr Cys Ile His
1               5                   10                  15
Gly Arg Cys Arg Phe Val Val Asp Glu Gln Thr Pro Ser Cys Ile Cys
            20                  25                  30
Glu Lys Gly Tyr Thr Gly Ala Arg Cys Glu Arg Val Asp Leu
        35                  40                  45
```

<210> SEQ ID NO 11
<211> LENGTH: 46
<212> TYPE: PRT
<213> ORGANISM: Mus musculus

<400> SEQUENCE: 11

```
Val Gln Ile Tyr Lys Cys Ser Ser Asp Met Asp Gly Tyr Cys Leu His
1               5                   10                  15
Gly Gln Cys Ile Tyr Leu Val Asp Met Arg Glu Lys Phe Cys Arg Cys
            20                  25                  30
Glu Val Gly Tyr Thr Gly Leu Arg Cys Glu His Phe Phe Leu
        35                  40                  45
```

<210> SEQ ID NO 12
<211> LENGTH: 46
<212> TYPE: PRT
<213> ORGANISM: Mus musculus

<400> SEQUENCE: 12

```
Lys Lys Arg Asp Pro Cys Leu Arg Lys Tyr Lys Asp Tyr Cys Ile His
1               5                   10                  15
```

```
Gly Glu Cys Arg Tyr Leu Gln Glu Phe Arg Thr Pro Ser Cys Lys Cys
            20                  25                  30

Leu Pro Gly Tyr His Gly His Arg Cys His Gly Leu Thr Leu
        35                  40                  45

<210> SEQ ID NO 13
<211> LENGTH: 46
<212> TYPE: PRT
<213> ORGANISM: Mus musculus

<400> SEQUENCE: 13

Lys Lys Lys Asn Pro Cys Thr Ala Lys Phe Gln Asn Phe Cys Ile His
1               5                   10                  15

Gly Glu Cys Arg Tyr Ile Glu Asn Leu Glu Val Val Thr Cys Asn Cys
            20                  25                  30

His Gln Asp Tyr Phe Gly Glu Arg Cys Gly Glu Lys Ser Met
        35                  40                  45

<210> SEQ ID NO 14
<211> LENGTH: 536
<212> TYPE: DNA
<213> ORGANISM: Homo sapiens

<400> SEQUENCE: 14
tcctactctc ttgaccaaga atgaaactat ttacaaatta agatgccaac agatcacgaa      60
gagccctgtg gtcccagtca caagtcgttt tgcctgaatg gggggctttg ttatgtgata     120
cctactattc ccagcccatt tgtaggtgc gttgaaaact atacaggagc tcgttgtgaa     180
gaggtttttc tcccaggctc cagcatccaa actaaaagta acctgtttga agcttttgtg     240
gcattggcgg tcctagtaac acttatcatt ggagccttct acttcctttg caggtgtggt     300
aacacatgca tgtagtccta gctgcttggg aggctgagat gggaagatcg cttgagccca     360
ggaatgagag gctgcagtta agccatgact gcactactgc actcctgcct gggaaaggcc     420
actttcagag agccagttca gtccagtatg atatcaacct ggtagagacg agcagtacca     480
gtgcccacca cagtcatgaa caacactgaa gaaacgtcaa agtgaaccaa atcatt        536

<210> SEQ ID NO 15
<211> LENGTH: 90
<212> TYPE: PRT
<213> ORGANISM: Homo sapiens

<400> SEQUENCE: 15

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Cys Gly Asn Thr Cys Met
                85                  90

<210> SEQ ID NO 16
<211> LENGTH: 26
<212> TYPE: DNA
```

```
<213> ORGANISM: Artificial Sequence
<220> FEATURE:
<223> OTHER INFORMATION: synthetic oligonucleotide

<400> SEQUENCE: 16
cctactctct tgaccaagaa tgaaac                                              26

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 17
aatgatttgg ttcactttga cg                                                 22

<210> SEQ ID NO 18
<211> LENGTH: 40
<212> TYPE: PRT
<213> ORGANISM: Artificial Sequence
<220> FEATURE:
<223> OTHER INFORMATION: motif consensus sequence
<221> NAME/KEY: misc_feature
<222> LOCATION: (2)..(8)
<223> OTHER INFORMATION: any amino acid
<221> NAME/KEY: misc_feature
<222> LOCATION: (10)..(10)
<223> OTHER INFORMATION: any amino acid
<221> NAME/KEY: misc_feature
<222> LOCATION: (14)..(14)
<223> OTHER INFORMATION: any amino acid
<221> NAME/KEY: misc_feature
<222> LOCATION: (16)..(28)
<223> OTHER INFORMATION: any amino acid
<221> NAME/KEY: misc_feature
<222> LOCATION: (30)..(30)
<223> OTHER INFORMATION: any amino acid
<221> NAME/KEY: misc_feature
<222> LOCATION: (32)..(34)
<223> OTHER INFORMATION: any amino acid
<221> NAME/KEY: misc_feature
<222> LOCATION: (36)..(36)
<223> OTHER INFORMATION: any amino acid
<221> NAME/KEY: misc_feature
<222> LOCATION: (38)..(38)
<223> OTHER INFORMATION: any amino acid

<400> SEQUENCE: 18

Cys Xaa Xaa Xaa Xaa Xaa Xaa Xaa Cys Xaa Asn Gly Gly Xaa Cys Xaa
1               5                   10                  15

Xaa Xaa Xaa Xaa Xaa Xaa Xaa Xaa Xaa Xaa Xaa Xaa Cys Xaa Cys Xaa
            20                  25                  30

Xaa Xaa Tyr Xaa Gly Xaa Arg Cys
        35                  40
```

POLYNUCLEOTIDES ENCODING A NOVEL GROWTH FACTOR WHICH ACTS THROUGH ERBB-4 KINASE RECEPTOR TYROSINE

FIELD AND BACKGROUND OF THE INVENTION

The present invention relates to a novel ErbB-4 ligand, referred to herein as Neuregulin-4 (NRG-4), to polynucleotide sequences encoding said NRG-4, to oligonucleotides and oligonucleotide analogs derived from said polynucleotide sequences, to a display library displaying short peptides derived from said NRG-4, to antibodies recognizing said NRG-4, to peptides or peptide analogs derived from said NRG-4, and to pharmaceutical compositions and methods of employing said peptides or peptide analogs, said oligonucleotides and oligonucleotide analogs, and/or said polynucleotide sequences to up-regulate or down-regulate ErbB-4 receptor activity.

Cell-to-cell signaling is an essential feature of multicellular organisms, playing important roles in both the unfolding of developmental diversification as well as mediating the homeostasis of vastly different cell types. A large number of tyrosine kinase growth factor receptors play key roles in this process. Type-1 tyrosine kinase receptors, also known as ErbB/HER proteins, comprise one of the better-characterized families of growth factor receptors, of which the epidermal growth factor receptor (ErbB-1) is the prototype [reviewed in (Burden & Yarden, 1997)]. The ErbB family constitutes four known receptors which dimerize upon ligand stimulation, transducing their signals by subsequent autophosphorylation catalyzed by an intrinsic cytoplasmic tyrosine kinase, and recruiting downstream signaling cascades.

The ErbB receptors are activated by a large number of ligands. Depending upon the activating ligand, most homodimeric and heterodimeric ErbB combinations can be stabilized upon ligand binding (Tzahar et al., 1996), thus allowing a complex, diverse downstream signaling network to arise from these four receptors. The choice of dimerization partners for the different ErbB receptors, however, is not arbitrary.

Spatial and temporal expression of the different ErbB receptors do not always overlap in vivo, thus narrowing the spectrum of possible receptor combinations that an expressed ligand can activate for a given cell type (Erickson et al., 1997; Gassmann et al., 1995; Lee et al., 1995; Pinkas-Kramarski et al., 1997; Riethmacher et al., 1997).

Furthermore, a hierarchical preference for signaling through different ErbB receptor complexes takes place in a ligand-dependent manner. Of these, ErbB-2-containing combinations are often the most potent, exerting prolonged signaling through a number of ligands, likely due to an ErbB-2-mediated deceleration of ligand dissociation (Karunagaran et al., 1996; Tzahar et al., 1996; Wang et al., 1998).

In contrast to possible homodimer formation of ErbB-1 and ErbB-4, for ErbB-2, which has no known direct ligand, and for ErbB-3, which lacks an intrinsic tyrosine kinase activity (Guy et al., 1994), homodimers either do not form or are inactive.

Heterodimeric ErbB complexes are arguably of importance in vivo. For example, mice defective in genes encoding either NRG-1, or the receptors ErbB-2 or ErbB-4, all result in identical failure of trabeculae formation in the embryonic heart, consistent with the notion that trabeculation requires activation of ErbB-2/ErbB-4 heterodimers by NRG-1 (Gassmann et al., 1995; Lee et al., 1995; Meyer & Birchmeier, 1995).

At the biochemical level, the known ErbB ligands fall into several categories (Riese et al., 1996b). One category, the ErbB-1 ligands, includes EGF, Transforming Growth Factor α (TGFα), Epiregulin, Amphiregulin, Betacellulin and the Heparin-binding EGF (HB-EGF) (Higashiyama et al., 1991; Marquardt et al., 1984; Shing et al., 1993; Shoyab et al., 1989; Toyoda et al., 1995). To different extents, these ErbB-1 binding ligands can also activate other receptors of the ErbB family, and hence may mediate distinct signaling outputs for a given cell type [reviewed in (Tzahar & Yarden, 1998)].

Another category of ErbB ligands comprises the Neuregulin (NRG) family. NRG-1 [also named Neu differentiation factor (NDF), Heregulin, Glial Growth factor, and Acetylcholine Receptor Inducing Activity] was first identified by its ability to indirectly phosphorylate ErbB-2 (Holmes et al., 1992; Peles et al., 1992; Wen et al., 1992). Subsequently, NRG-1 was found to directly bind ErbB-3 and ErbB-4 and to sequester ErbB-2 by receptor dimerization (Peles et al., 1993; Plowman et al., 1993; Sliwkowski et al., 1994; Tzahar et al., 1994). Multiple isoforms of NRG-1 exist which amongst other roles, permit heterogeneous binding affinities to different ErbB complexes (Tzahar et al., 1994). The NRG family now includes also two isoforms of NRG-2 (Busfield et al., 1997; Carraway et al., 1997; Chang et al., 1997; Higashiyama et al., 1997), of which the alpha isoform is a pan-ErbB ligand (Pinkas-Kramarski et al., 1998), and NRG-3, a ligand of ErbB-4 (Zhang et al., 1997).

The multiplicity of genes encoding ErbB-1 ligands, contrasting with the small number of known genes encoding ligands for ErbB-3 or ErbB-4 (namely: NRGs), led the inventors of the present invention to believe in the existence of additional NRG genes in the genome of mammals.

A fourth Neuregulin, denoted NRG-4, which acts through the ErbB-4 receptor tyrosine kinase is reported herein. In addition to its novel structure, this growth factor displays a pattern of expression different from other EGF-like molecules.

SUMMARY OF THE INVENTION

Thus, the ErbB/HER family of receptor tyrosine kinases include four receptors that bind a large number of growth factor ligands sharing an epidermal growth factor (EGF)-like motif. Whereas ErbB-1 binds seven different ligands whose prototype is EGF, the three families of Neuregulins (NRGs) bind ErbB-3 and/or ErbB-4. While reducing the present invention to practice a fourth neuregulin, NRG-4, that acts through ErbB-4, has been identified, isolated and characterized. The predicted pre-NRG-4 is a transmembrane protein carrying a unique EGF-like motif and a short cytoplasmic domain. A synthetic peptide encompassing the full-length EGF-like domain induces growth of interleukin-dependent cells ectopically expressing ErbB-4, but not cells expressing the other three ErbB proteins or their combinations. Consistent with specificity to ErbB-4, NRG-4 can displace an ErbB-4-bound NRG-1 and can activate signaling downstream of this receptor. Expression of NRG-4 mRNA was detected in the adult pancreas and weakly in muscle. The primary structure and the pattern of expression of NRG-4, together with the strict specificity of this growth factor to ErbB-4, suggest a physiological role distinct to that of the known ErbB ligands. This strict specificity of binding can be exploited in numerous biopharmaceutical purposes.

According to one aspect of the present invention there is provided an isolated nucleic acid comprising a geonomic, complementary or composite polynucleotide sequence encoding a polypeptide being capable of binding to a mammalian ErbB-4 receptor and including a stretch of amino acids at least 95% homologous to a stretch of amino acids derived from SEQ ID NO:15 as determined using the BestFit software of the Wisconsin sequence analysis package, utilizing the Smith and Waterman algorithm, where gap creation penalty equals 8 and gap extension penalty equals 2.

According to another aspect the polynucleotide encodes a polypeptide which is at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to preferred embodiments, the polynucleotide according to this aspect of the present invention encodes a polypeptide as set forth in SEQ ID NOs:2 or 15 or a portion thereof, preferably a portion which retains the binding activity.

According to still preferred embodiments, the polynucleotide according to this aspect of the present invention includes a polynucleotide stretch at least 80% identical to positions 55–190 of SEQ ID NO:14 as determined using the BestFit software of the Wisconsin sequence analysis package, utilizing the Smith and Waterman algorithm, where gap weight equals 50, length weight equals 3, average match equals 10 and average mismatch equals −9.

Alternatively or additionally, the polynucleotide according to this aspect of the present invention is preferably hybridizable with SEQ ID NOs:1 or 14.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and 5×10$^6$ cpm $^{32}$p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 50° C.

Yet alternatively or additionally, the polynucleotide according to this aspect of the present invention is preferably at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to preferred embodiments the polynucleotide according to this aspect of the present invention is as set forth in SEQ ID NOs:1 or 14 or a portion thereof, said portion preferably encodes a polypeptide retaining the binding activity.

According to another aspect of the present invention there is provided a nucleic acid construct comprising the isolated nucleic acid described herein. According to a preferred embodiment the nucleic acid construct according to this aspect of the present invention further comprising a promoter for regulating expression of the isolated nucleic acid in a sense of antisense orientation.

Alternatively, the nucleic acid construct according to this aspect of the present invention further comprising a positive and a negative selection markers and may therefore be employed for selecting homologous recombination events, including, but not limited to, homologous recombination employed in knock-in and knock-out procedures.

Consequently, according to yet another aspect of the present invention there is provided a host cell or animal comprising a nucleic acid construct as described herein.

According to still another aspect of the present invention there is provided an oligonucleotide of at least 17 bases specifically hybridizable with the isolated nucleic acid described herein.

Hybridization of shorter nucleic acids (below 200 bp in length, e.g. 17–40 bp in length) is effected by stringent, moderate or mild hybridization, wherein stringent hybridization is effected by a hybridization solution of 6×SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1–1.5° C. below the $T_m$, final wash solution of 3 M TMACI, 0.01 M sodium phosphate (pH 6.8), 1 mM EDTA (pH 7.6), 0.5% SDS at 1–1.5° C. below the $T_m$; moderate hybridization is effected by a hybridization solution of 6×SSC and 0.1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2–2.5° C. below the $T_m$, final wash solution of 3 M TMACI, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of a hybridization solution of 6×SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each of at least 17 bases specifically hybridizable with the isolated nucleic acid described herein in an opposite orientation so as to direct exponential amplification of a portion thereof in a nucleic acid amplification reaction.

According to yet an additional aspect of the present invention there is provided a nucleic acid amplification product obtained using the pair of primers described herein.

According to still an additional aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to a further aspect of the present invention there is provided a pharmaceutical composition comprising the antisense oligonucleotide described herein and a pharmaceutically acceptable carrier.

According to still a further aspect of the present invention there is provided a ribozyme comprising the antisense oligonucleotide described herein and a ribozyme sequence fused thereto.

According to yet a further aspect of the present invention there is provided a recombinant or synthetic protein comprising a polypeptide being capable of binding to a mammalian ErbB-4 receptor and including a stretch of amino acids at least 95% homologous to a stretch of amino acids derived from SEQ ID NO:15 as determined using the BestFit software of the Wisconsin sequence analysis package, utilizing the Smith and Waterman algorithm, where gap creation penalty equals 8 and gap extension penalty equals 2. Most preferably the polypeptide includes at least a portion of SEQ ID NOs:2 or 15. Additionally or alternatively, the polypeptide according to this aspect of the present invention is preferably encoded by a polynucleotide hybridizable with SEQ ID NOs:1 or 14 or a portion thereof under any of the stringent or moderate hybridization conditions described above for long nucleic acids. Still additionally or alternatively, the polypeptide according to this aspect of the present invention is preferably encoded by a polynucleotide at least 50% identical with SEQ ID NOs:1 or 14 or portions thereof as determined using the BestFit software of the Wisconsin sequence analysis package, utilizing the Smith and Waterman algorithm, where gap weight equals 50, length weight equals 3, average match equals 10 and average mismatch equals −9.

According to still a further aspect of the present invention there is provided a pharmaceutical composition comprising, as an active ingredient, the recombinant protein described herein and a pharmaceutical acceptable carrier.

According to another aspect of the present invention there is provided a peptide or a peptide analog comprising a stretch of at least 6 consecutive amino acids or analogs thereof derived from a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the peptide or a peptide analog according to this aspect of the present invention comprises a stretch of at least 6 consecutive amino acids or analogs thereof derived from SEQ ID NOs:2 or 15.

According to still another aspect of the present invention there is provided a display library comprising a plurality of display vehicles (such as phages, viruses or bacteria) each displaying at least 6 consecutive amino acids derived from a polypeptide at least 50% homologous to at least positions 4–50 of SEQ ID NOs:2 or 15 as determined using the BestFit software of the Wisconsin sequence analysis package, utilizing the Smith and Waterman algorithm, where gap creating penalty equals 8 and gap extension penalty equals 2. According to a preferred embodiment of this aspect of the present invention substantially every 6 consecutive amino acids derived from the polypeptide are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:2 or 15.

According to still another aspect of the present invention there is provided an antibody comprising an immunoglobulin specifically recognizing a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention the antibody specifically recognizing the polypeptides set forth in SEQ ID NOs:2 or 15. The antibody according to this aspect of the present invention can be, for example, a polyclonal antibody, a monoclonal antibody, a humanized antibody, a single chain antibody or an immunoreactive derivative (e.g., portion) of an antibody.

According to yet another aspect of the present invention there is provided a pharmaceutical composition comprising, as an active ingredient, an agent for regulating an endogenous protein affecting ErbB-4 activity, the endogenous protein being at least 50% homologous to at least positions 4–50 of SEQ ID NOs:1 or 15 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein activity affecting ErbB-4 activity the method comprising the steps of administering an agent for regulating the endogenous protein activity, the endogenous protein being at least 50% homologous to at least positions 4–50 of SEQ ID NOs:1 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent serves for altering, e.g., upregulating, the activity.

According to still further features in the described preferred embodiments the agent includes an expressible sense polynucleotide at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent serves for downregulating the activity.

According to still further features in the described preferred embodiments the agent includes an expressible antisense polynucleotide at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes an antisense oligonucleotide which includes a polynucleotide or a polynucleotide analog of at least 10 bases which is hybridizable in vivo, under physiological conditions, with a portion of a polynucleotide strand encoding a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent includes a peptide or a peptide analog representing a stretch of at least 6 consecutive amino acids or analogs thereof derived from a polypeptide at least 50% homologous to at least positions 4–50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

The present invention successfully addresses the shortcomings of the presently known configurations by disclosing a novel Neuregulin which specifically binds ErbB-4 with somewhat lower affinity as is compared to, for example, NRG-1β. Additional advantages, novel features and utilities of the various aspects of the present invention are described in the following sections of this application.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a shows the nucleotide sequence (SEQ ID NO:1) and deduced amino acid sequence (SEQ ID NO:1) of mouse pro-NRG-4. Nucleotides are numbered at the left-hand column and amino acids at the right hand column. The EGF-like domain with its six cysteine residues is shown in bold type, and potential N-glycosylation sites are underlined. The filled box underlines the predicted transmembrane amino acid sequence.

FIG. 1b shows the hydropathy profile of mouse pro-NRG-4. The method of Kyte and Doolittle (Kyle & Doolittle, 1982) was used with a window of 11 residues. Positive values indicate increasing hydrophobicity. Amino acid numbers are indicated below the profile. The putative transmembrane stretch of the pro-NRG-4 is marked. Note the absence of a recognizable signal peptide at the N-terminus.

FIG. 1c shows alignment of mouse amino acid sequence of the EGF-like domain of NRG-4 with the EGF-like motifs of other growth factors (SEQ ID NOs:3–13 as indicated in the Figure). Canonical residues are boxed in black. Other identities with NRG-4 are shaded in gray. The predicted three disulfide bonds of the motifs (Cys 1–3, Cys 2–4, and Cys 5–6) are shown above the alignment and labeled as loops A, B and C. The abbreviations used are as follows: NRG, Neuregulin; TGFα, Transforming Growth Factor α; HB-EGF, Heparin-Binding EGF-like Growth Factor. If not specified, the species of origin of all ligands is murine, except NRG-1β (rat). For alignment, the FastA (Pearson and Lipman) search was employed with the following search parameters, word size of 2, Scoring matrix—blosum 50, Variable pamfactor used—Gap creation penalty: 12, Gap extension penalty: 2, Joining threshold: 36, opt. threshold: 24, and opt. width: 16.

FIG. 1e shows the nucleotide sequence (SEQ ID NO:14) and deduced amino acid sequence (SEQ ID NO:15) of human NRG-4 and its comparison with the nucleotide sequence (SEQ ID NO:1) and deduced amino acid sequence (SEQ ID NO:2) of mouse NRG-4. Human NRG-4, derived from T47D cells was sequenced from two independent RT-PCR reactions and compared to the mouse sequence. The predicted EGF-encoding domains and transmembrane domains are marked in bold and are underlined respectively. Shaded boxes indicate protein sequence identity. The predicted translation products share 78% overall identity and 91% sequence identity within the EGF-like encoding domain.

DESCRIPTION OF THE PREFERRED EMBODIMENTS

Figure 1D:
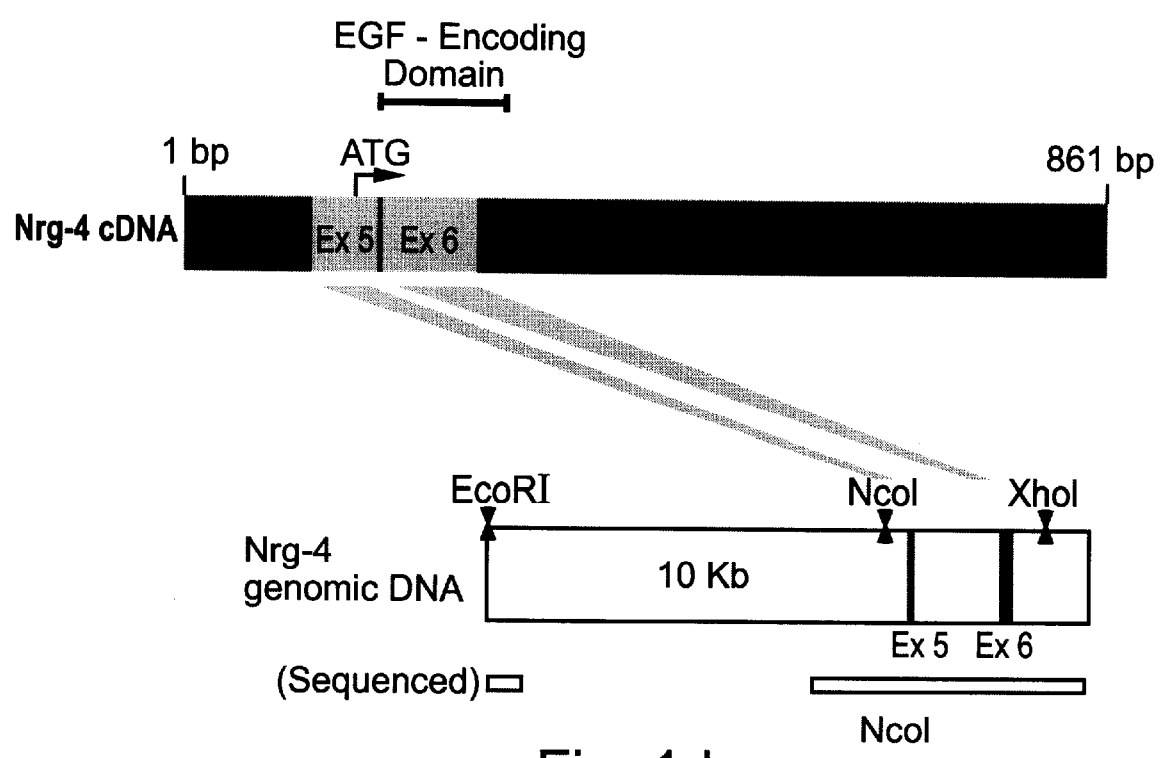
FIG. 1d shows the mouse NRG-4 gene structure. The mouse genomic NRG-4 was isolated from a PBAC library using the EGF-encoding domain as a probe. An EcoR1 digested subclone is depicted, with sequenced regions underlined in shade. Two exons found in the genomic sequence were arbitrarily designated as Exons 5 and 6 (Ex 5 & Ex 6), in accordance with the prototypical NRG-1 genetic structure, in which the invariant component of the EGF-domain is also designated as "Exon 6" (Ex 6). The intron-exon boundaries of Ex 6 for both NRG-1 and NRG-4 are identical, supporting the idea that these genes are derived from a common ancestor, and further supports that NRG-4 is a novel variant of the Neuregulin gene family.

The present invention is of (i) a novel Neuregulin which is referred to herein as NRG-4; (ii) polynucleotide sequences encoding NRG-4; (iii) oligonucleotides and oligonucleotide analogs derived from said polynucleotide sequences; (iv) a display library displaying short peptides derived from said NRG-4; (v) antibodies recognizing said NRG-4; (vi) peptides or peptide analogs derived from said NRG-4; and (vii) pharmaceutical compositions; and (viii) methods of employing said peptides or peptide analogs, said oligonucleotides and oligonucleotide analogs, and/or said polynucleotide sequences to up-regulate or down-regulate ErbB-4 activity.

The principles operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or exemplified in the Examples section that follows. The invention is capable of other embodiments or of being practiced or carried out in various ways. Also, it is to be understood that the phraseology and terminology employed herein is for the purpose of description and should not be regarded as limiting.

While conceiving the present invention it was hypothesized that additional, yet unknown, ErbB tyrosine kinase receptor ligands may exist. Screening an EST database with the motif $CX_7CXNGGXCX_{13}CXCX_3YXGXRC$ (SEQ ID NO:18), which is conserved in most ErbB-ligand isoforms, revealed (i) an EST clone originating from a mouse liver cDNA library (accession number AA238077) encoding an EGF-like domain sharing 32% identity with the NRG-1β isoform (Wen et al., 1992); and (ii) a human derived EST clone (accession No. A1743118) having an EGF-like domain disrupted by an insert.

While reducing the present invention to practice these clones have been characterized as encoding yet unknown ligands of the EGF/NRG family, which was referred to as Neuregulin-4 (NRG-4). Aside from NRG-4 possessing a Neuregulin-like EGF domain (FIG. 1c), it shares very little other sequence homology to the known NRGs (NRG-1 through 3), particularly in the vicinity of the transmembrane domain, a region where the other three NRGs exhibit high primary sequence homology. However, the presumed precursor form of NRG-4 shares several structural characteristics with other mammalian ErbB ligands [which are reviewed in (Massague & Pandiella, 1993)], including a transmembrane topology, a juxtamembrane location of the EGF-like domain, and a putative proteolytic cleavage site located at a serine-rich region C-terminally to the EGF-like domain. This region may serve as a site of O-glycosylation, in addition to two potential sites of N-glycosylation located in the presumed ectodomain of NRG-4. Like other NRGs, but unlike most ErbB-1-specific ligands, NRG-4 lacks an N-terminally located hydrophobic signal peptide. However, the absence of a characteristic sequence may not exclude the possibility that NRG-4 acts as a secreted growth factor, because other signal peptide-less growth factors can be secreted or released from producer cells through alternative secretory mechanisms or upon cell lysis. NRG-4 presents a rather unique case as it also lacks an apolar stretch of amino acids that usually replaces a signal peptide (e.g., in NRG-1). In fact, the presumed ectodomain of NRG-4 is the shortest among NRG/EGF family members. In addition, unlike other NRGs, which contain a variety of structural motifs, such as an immunoglobulin-like domain, a cysteine-rich region, or a mucin-like domain, NRG-4 contains no recognizable structural motif other than the EGF-like domain.

Interspecies conservation of NRG-4 was identified by comparison between human and mouse NRG-4 cDNAs. The human and mouse cDNA sequences share 78% overall identity and 91% sequence identity demonstrating that NRG-4 is expressed amongst mammals and the high interspecies homology particularly within the EGF-domain indicates an important physiological role for this gene.

The prototypical NRG-1 gene encodes a large number of isoforms (Baruch & Yarden, 1994). However the ErbB-binding moiety of NRG-1 is defined by the EGF-encoding domain, of which there are only two variants (alpha and beta). The two NRG-1 EGF-domain encoded variants share an invariant $NH_3$ component encoded by Exon 6 and two alternative COOH-termini generated by subsequent alternative exon splicing. By analogy, the mouse NRG-4 genomic locus shares the same genomic exon-intron structure spanning Exon-6. This finding not only supports that NRG-4 is ancestrally related to NRG-1, it also strengthens the suspicion that the NRG-4 locus may encode many isoforms, including perhaps two variants of the EGF-like domain. Indeed, Northern Blot analysis revealed the presence of distinctive bands hybridizing to NRG-4, demonstrating that isoforms of differing size are likely to exist. Many or all of these isoforms will harbor the EGF-domain reported in this study and will elicit the identical ErbB-binding moieties as that for this novel ligand.

Figure 3A:
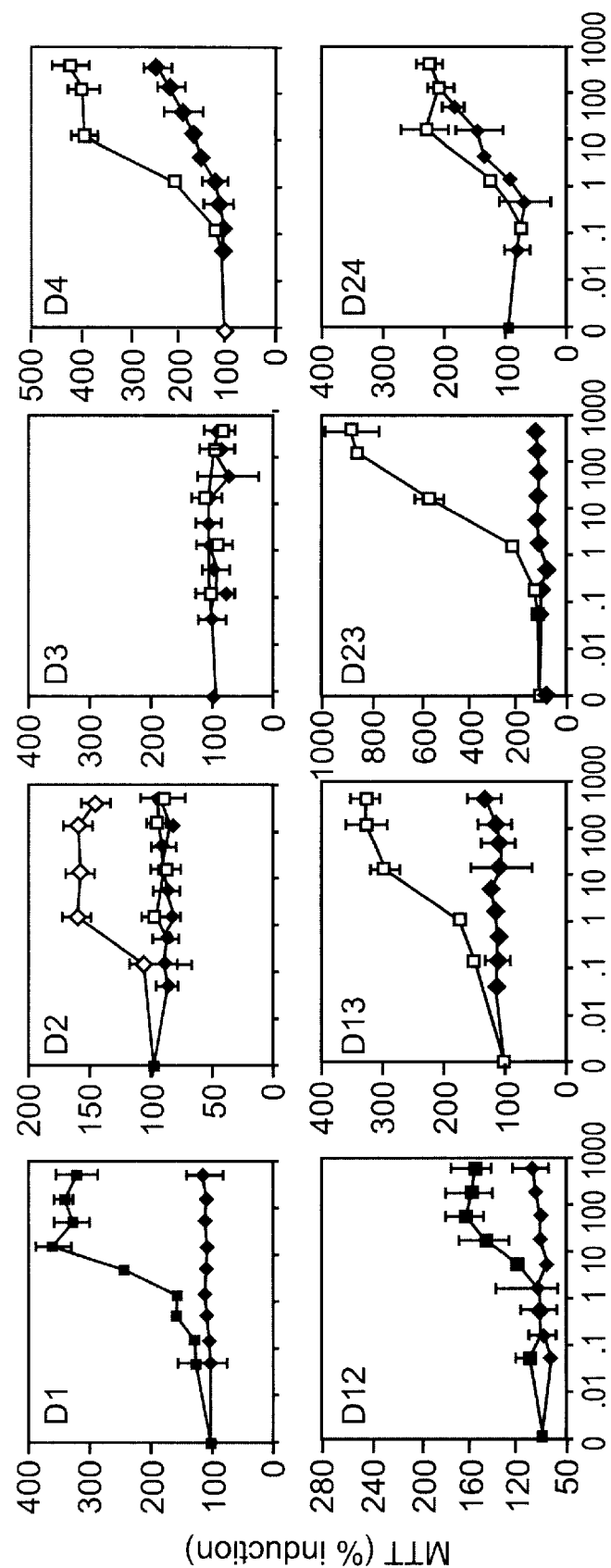
FIG. 3a shows proliferative effect of NRG-4 on ErbB-expressing derivatives of 32D cells. The indicated derivative lines of 32D cells were tested for cell proliferation using the [3-(4,5-dimethylthiazol-2-yl)-2,5-diphenyl] retrazolium bromide (MTT) assay. Cells were deprived of serum factors and IL-3 and then plated at a density of $5 \times 10^5$ cells/ml in media containing serial dilutions of NRG-4 (closed diamonds), EGF (closed squares), NRG-1β (open squares), or the L96 (maximal dose: 50 μg/ml) anti-ErbB-2 monoclonal antibody (open diamonds). The MTT assay was performed 24 hours later. Results are presented as percent induction over the control untreated cells, and are the mean ± S.D. of 4 determinations. Each experiment was repeated at least twice with similar findings. Note that no responses to EGF-like ligands were observed with cells expressing either ErbB-2 or ErbB-3 alone, but these cell derivatives retained response to IL-3 (data not shown).
Figure 3B:
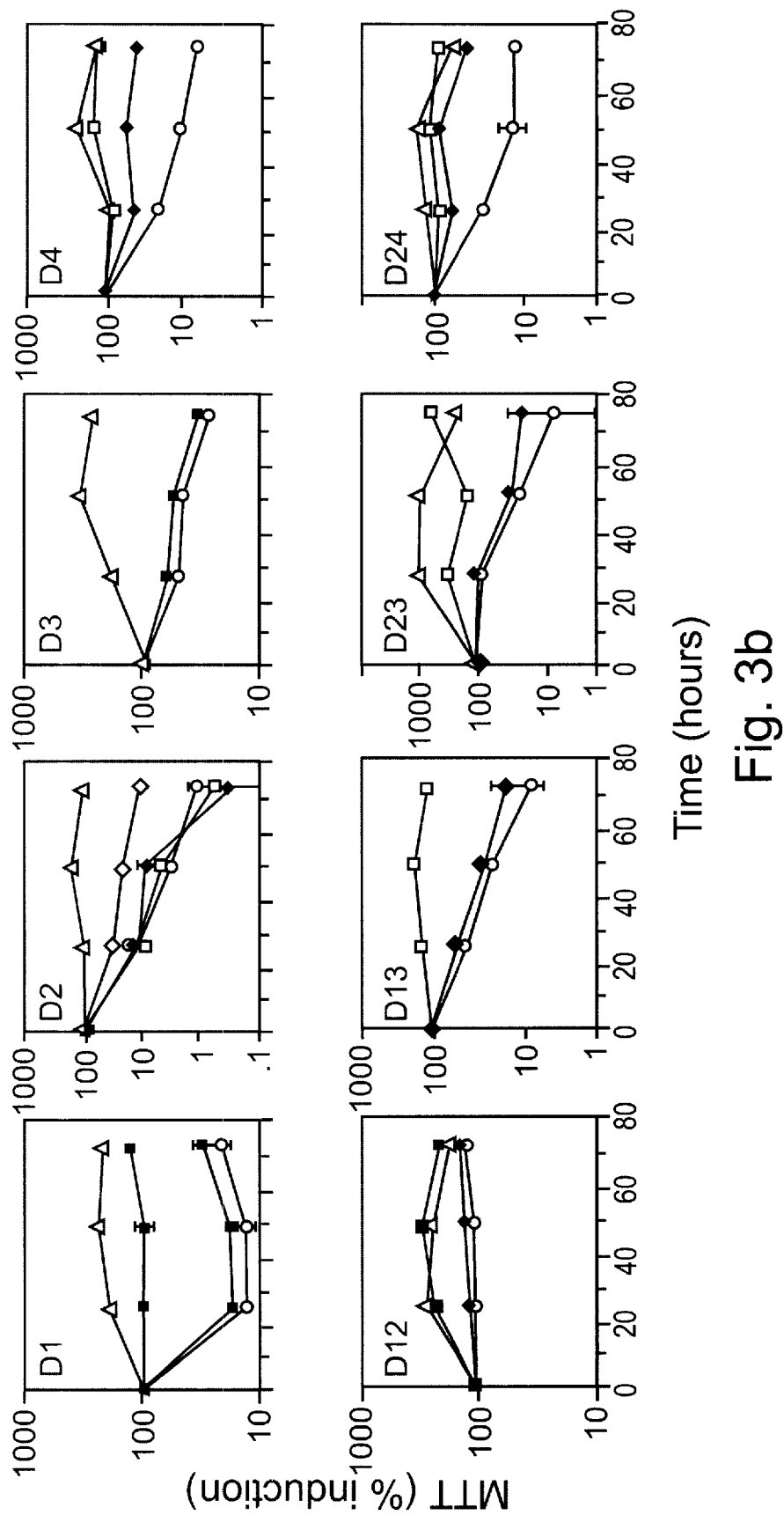
FIG. 3b show survival effect of NRG-4 on ErbB-expressing derivatives of 32D cells. The indicated derivatives of 32D cells were incubated for various time intervals in the absence of IL-3. The following ligands, each at a concentration of 100 ng/ml, were incubated with cells: NRG-4 (closed diamonds), EGF (closed squares), NRG-1β (open squares), or 50 μg/ml mAb L96 (open diamonds). For control, cells were incubated with medium conditioned by IL-3-producing cells (open triangles), or with no factor (open circles). The extent of cell proliferation was determined daily by using the colorimetric MIT assay. The data presented are the mean ± S.D. of 4 determinations. Note that co-expression of ErbB-1 and ErbB-2 (D12 cells) enabled cell survival in the absence of IL-3. The experiment was repeated twice with similar results.
Figure 4A:
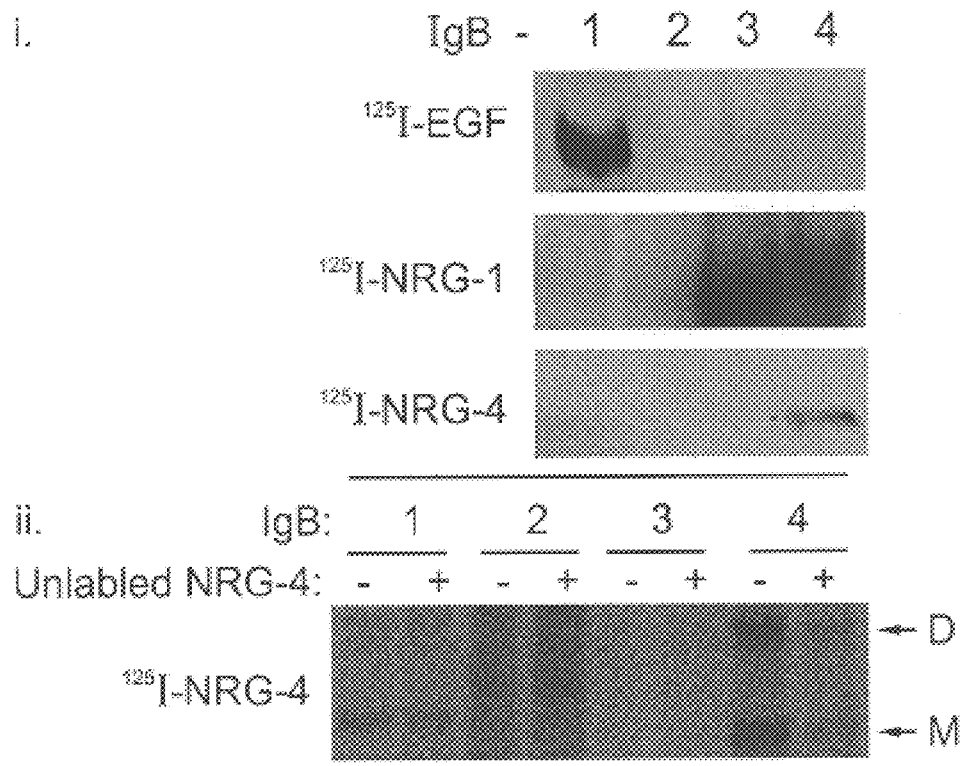
FIG. 4a shows covalent crosslinking of NRG-4 to recombinant-soluble ErbB proteins. The four soluble forms of ErbB proteins, in the form of IgG fusions (denoted IgB-1 through 4), were separately incubated with the indicated radiolabeled growth factors. Where indicated (lower panel), an excess (100-fold) of unlabeled NRG-4 was co-incubated with the labeled ligand. Following 2 hours at 22° C., the covalent crosslinking reagent bis(sulfosuccinimdyl)-suberate ($BS^3$) was added (1 mM) and 45 minutes later the ligand-receptor complexes were immunoprecipitated with agarose-immobilized protein-A beads. Arrows mark the locations of monomeric (M) and dimeric (D) receptor complexes.
Figure 4B:
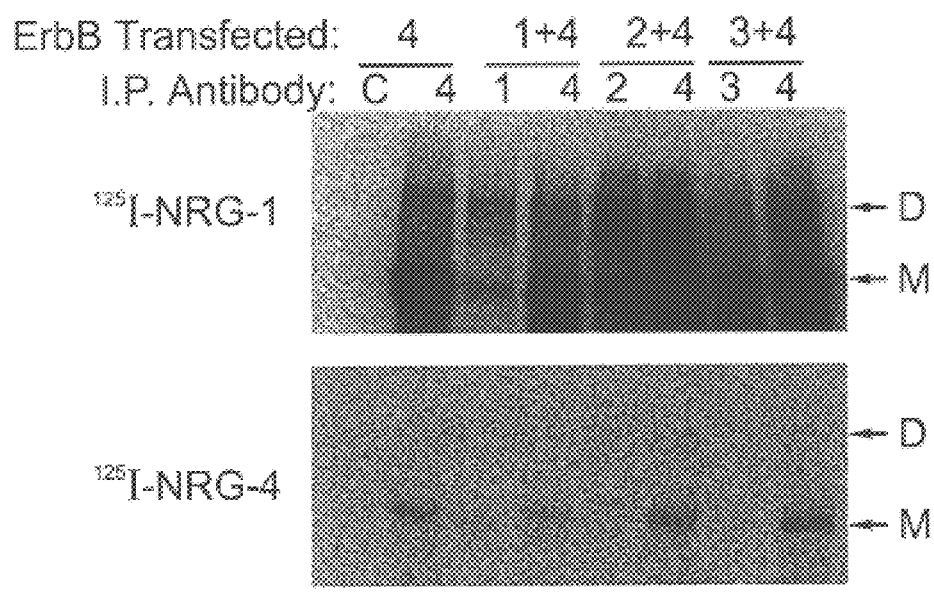
FIG. 4b shows covalent crosslinking of NRG-4 to cell surface-expressed ErbB proteins. CHO cells were transfected with vectors directing expression of the indicated ErbB proteins or their combinations. Two days later cell monolayers were incubated with either $^{125}$I-NRG-1β or $^{125}$I-NRG-4 (EGF-like domains, each at 100 ng/ml). Following 2 hours at 4 C, the covalent crosslinking reagent bis(sulfosuccinimdyl)-suberate ($BS^3$) was added (1 mM final concentration) and cell extracts prepared after an additional 45 minutes of incubation. The indicated ErbB proteins were then immunoprecipitated with mouse monoclonal antibodies, and the complexes resolved by gel electrophoresis and autoradiography. Arrows mark the locations of monomeric (M) and dimeric (D) receptor complexes.
Figure 4C:
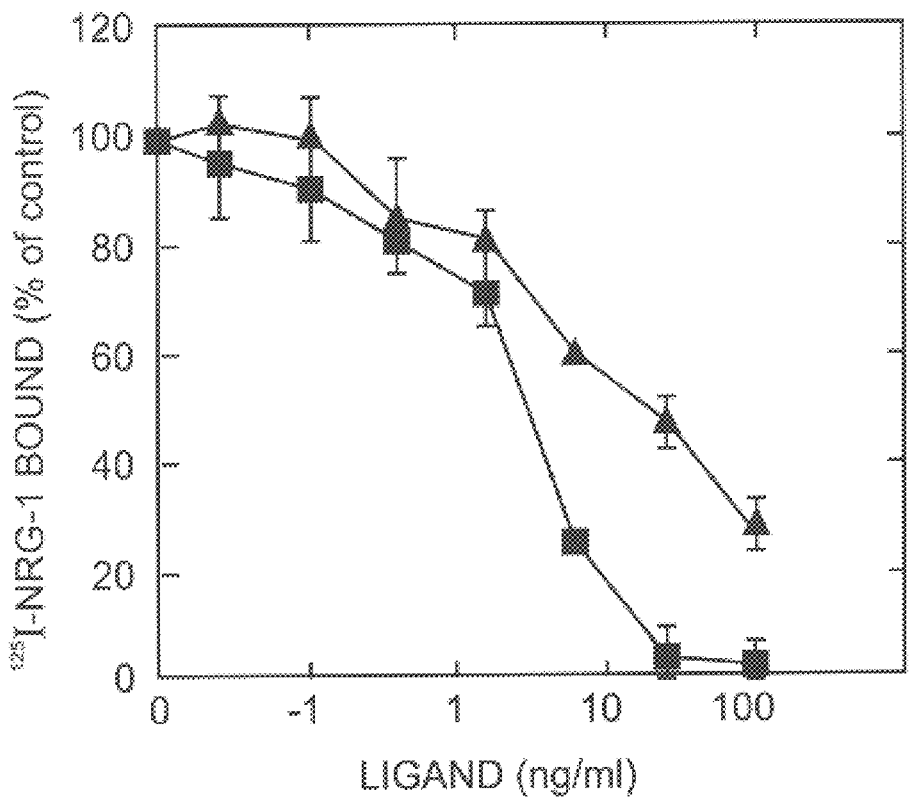
FIG. 4c shows binding of NRG-4 to ErbB-4-expressing cells. Displacement analyses of radiolabeled NRG-1β were performed with CHO cells expressing ErbB-4. Cell monolayers ($2 \times 10^5$ cells) were incubated for 2 hours at 4° C. with a radiolabeled NRG-1β (5 ng/ml) in the presence of increasing concentrations of an unlabeled NRG-4 (closed triangles), or NRG-1β (closed squares). Each data point represents the mean and range (bars) of two determinations.
Figure 5:
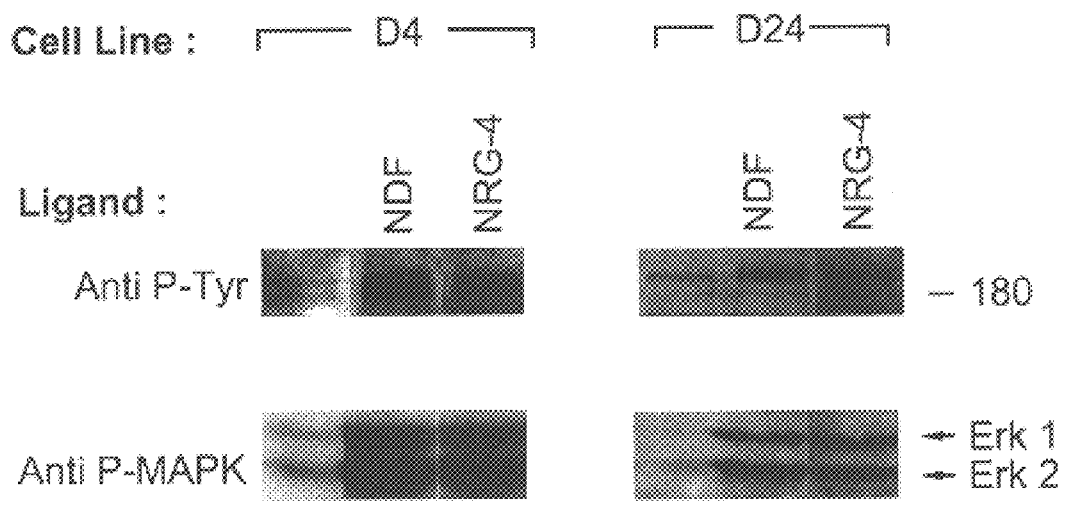
FIG. 5 shows tyrosine phosphorylation and MAPK activation by NRG-4. Derivatives of 32D cells expressing ErbB-4, either alone (D4 cells) or in combination with ErbB-2 (D24 cells) were incubated for 5 minutes at 37° C. with either NRG-4 or NRG-1β (each at 100 ng/ml). Whole cell extracts were then prepared, resolved by gel electrophoresis, and transferred to a nitrocellulose filter. The upper portion of the filter was immunoblotted with antibodies to phosphotyrosine (P-Tyr, the 150–200 kDa region is shown) or an antibody directed at the activated doubly phosphorylated form of the MAPK (Erk1 and Erk2, the 40–50 kDa region is shown). Antibodies were incubated with a secondary reagent coupled to horseradish peroxidase, allowing subsequent detection by chemiluminescence.

That the EGF-like domain of NRG-4 functions as a receptor-binding moiety is indicated by in vitro studies with engineered cell lines expressing all four ErbB proteins (e.g., FIGS. 3 to 5). The EGF-like domain of NRG-4 exhibits restricted binding specificity; it directly binds to ErbB-4, but not to ErbB-1, ErbB-2 or ErbB-3. A similar selective binding to ErbB-4 has also been reported for NRG-3 (Zhang et al., 1997) and may indicate that during development and in the adult, ligands with restricted ErbB specificities may play important roles. It is interesting to note that NRG-3 is the EGF-like ligand closest to NRG-4 (42% sequence identity in the EGF-like domain). Also relevant is the emerging wider repertoire of ErbB-4-specific ligands, as compared with growth factors that bind to ErbB-3. In addition to NRG-1, NRG-2, and NRG-3, ErbB-4 also binds to betacellulin (Riese et al., 1996a), epiregulin (Shelly et al., 1998) and HB-EGF (Elenius et al., 1997). Moreover, at high ligand concentrations, or in the presence of a co-expressed ErbB-2, ErbB-4 also binds EGF and TGFα (Shelly et al., 1998; Wang et al., 1998). The broader specificity of ErbB-4 was reflected also in mutagenesis experiments: more NRG-1 mutants displayed greater affinity loss for ErbB-3 compared with ErbB-4 (Jones et al., 1998).

Besides specificity to ErbB-4, NRG-3 and NRG-4 share relatively low affinity to this receptor compared with NRG-1 [FIG. 4, and (Zhang et al., 1997)]. Several other ligands, such as epiregulin (Shelly et al., 1998) and the alpha isoform of NRG-1 (Tzahar et al., 1994), also display relatively low affinity to ErbB-4. These observations may suggest the existence of additional, yet undiscovered ErbB proteins, serving as high affinity receptors for these low affinity ligands. Alternatively, low affinity ligands may have a different biological function than high affinity growth factors, as they can escape the common rapid endocytic clearance from the extracellular space (Reddy et al., 1996; Shelly et al., 1998). Alternatively, the ligand-less co-receptor of ErbB-4, namely ErbB-2 (Karunagaran et al., 1996), may be more effective in the case of low affinity ligands, such as NRG-3 and NRG-4, thus offering a mechanism for fine-tuning of ErbB signaling. The interaction of ErbB ligands with ErbB-2 appears to involve direct binding to an ErbB-2 promiscuous binding site (Klapper et al., 1997; Tzahar et al., 1997). According to this model, all EGF-like growth factors are bivalent ligands, that differ in their binding specificity to specific pairs of ErbB receptors (Tzahar et al., 1997). This hypothesis may explain the multiplicity of ErbB ligands in terms of their differential ability to stabilize homo- and hetero-dimeric ErbB proteins. When applied to NRG-4, the bivalence model predicts that this ligand may differ from other ErbB-4-specific ligands, including NRG-3, in the ability to recruit heterodimer partners to ErbB-4.

Consistent with this model, it was demonstrated that when co-expressed with ErbB-4, NRG-4 can recruit both ErbB-1 and ERbB-2 into heterodimers (FIG. 4b). These NRG-4-induced heterodimeric complexes may be of physiological importance, as indicated in proliferation assays: NRG-4 weakly stimulated the growth of myeloid cells engineered to express ErbB-4 alone (D4 cells). In contrast, this response was significantly enhances upon ErbB-2 co-expression (D24 cells, FIGS. 3a–b) when compared to that of the internal NRG-1 control. This finding may indicate that under some physiological conditions, the expression of ErbB-4 alone may be insufficient to elicit a biological response to NRG-4, requiring a co-receptor such as ErbB-2 to transduce its signal. This scenario has a precedence in the case of NRG-1: in vitro experiments showed clear enhancement of an ErbB-4-mediated mitogenic effect by a co-expressed ErbB-2 (Wang et al., 1998), and gene-targeting in mice indicated that ErbB-2 is essential for cardiac trabeculation that is mediated by NRG-1 and ErbB-4 (Lee et al., 1995).

With the exception of EGF, which is found in high concentrations in body fluids such as milk, urine and saliva (Carpenter & Cohen, 1979; Gregory et al., 1979), all of the EGF/NRG family members are thought to act as short-range ligands affecting only neighboring cells through paracrine or autocrine loops [reviewed in (Ben-Baruch et al., 1998)]. Consistent with short-range ligand-receptor interactions, NRG-3 is expressed primarily in the central nervous system, along with its only known receptor, ErbB-4 (Plowman et al., 1993; Zhang et al., 1997). However, ErbB-4 is expressed also in muscle, heart, pancreas, salivary gland and lung (Gassmann et al., 1995; Pinkas-Kramarski et al., 1997; Plowman et al., 1993). A Northern blot analysis (FIG. 2) demonstrated that in the adult, two of these ErbB-4-positive tissues, pancreas and muscle, express three molecular weight mRNA species of NRG-4. Likewise, multiple mRNA species of NRG-1 and NRG-2 were reported (Chan et al., 1995; Wen et al., 1992). It is know in this respect that many isoforms of NRG-1 and NRG-2 (Busfield et al., 1997; Carraway et al., 1997; Chang et al., 1997; Marchionni et al., 1993; Wen et al., 1994) are derived from multiplicity of alternatively spliced NRGs mRNAs.

Thus, according to one aspect of the present invention there is provided an isolated nucleic acid comprising a genomic, complementary or composite polynucleotide sequence encoding a polypeptide being capable of binding to a mammalian ErbB-4 receptor which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% homologous (similar+identical acids) to SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the polypeptide being capable of binding to a mammalian ErbB-4 receptor according to the present invention includes a stretch of amino acids at least 90%, at least 91%, at least 92%, at least 93%, at least 94%, at least 95%, at least 96%, at least 97%, at least 98%, at least 99% or 100% homologous to a stretch of amino acids derived from SEQ ID NO:15 (e.g., amino acids 4–50 which form the EGF-like domain) as determined using the BestFit software of the Wisconsin sequence analysis package, utilizing the Smith and Waterman algorithm, where gap creation penalty equals 8 and gap extension penalty equals 2.

As used herein in the specification and in the claims section that follows, the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification and in the claims section that follows, the phrase "genomic polynucleotide sequence" includes sequences which originally derive from a chromosome and reflect a contiguous portion of a chromosome.

As used herein in the specification and in the claims section that follows, the phrase "composite polynucleotide sequence" includes sequences which are at least partially complementary and at least partially genomic. A composite sequence can include some exonal sequences required to encode a polypeptide, as well as some intronic sequences interposing therebetween. The intronic sequences can be of any source, including of other genes, and typically will include conserved splicing signal sequences. Such intronic sequences may further include cis acting expression regulatory elements.

According to preferred embodiments, the polynucleotide according to this aspect of the present invention encodes a polypeptide as set forth in SEQ ID NOs:2 or 15 or a portion thereof, preferably a portion which retains binding to ErbB-4 receptor, e.g., amino acids 4–50.

In a preferred embodiment the polynucleotide according to this aspect of the present invention includes a polynucleotide stretch at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to positions 55–190 of SEQ ID NO:14 as determined using the BestFit software of the Wisconsin sequence analysis package, utilizing the Smith and Waterman algorithm, where gap weight equals 50, length weight equals 3, average match equals 10 and average mismatch equals –9.

Alternatively or additionally, the polynucleotide according to this aspect of the present invention is preferably hybridizable with SEQ ID NOs: 1 or 14.

Hybridization for long nucleic acids (e.g., about 200 by in length) is effected according to preferred embodiments of the present invention by stringent or moderate hybridization, wherein stringent hybridization is effected by a hybridization solution containing 10% dextrane sulfate, 1 M NaCl, 1% SDS and 5×10⁶ rpm ³²p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and 5×10⁶ cpm ³²p labeled probe, at 65° C., with a final wash solution of 1×SSC and 0.1% SDS and final wash at 50° C.

Yet alternatively or additionally, the polynucleotide according to this aspect of the present invention is preferably at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals –9.

According to preferred embodiments the polynucleotide according to this aspect of the present invention is as set forth in SEQ ID NOs:1 or 14 or a portion thereof, said portion preferably encodes a polypeptide retaining the binding activity to ErbH-4.

Thus, this aspect of the present invention encompasses (i) polynucleotides a; set forth in SEQ ID NOs:1 or 14; (ii) fragments thereof; (iii) sequences hybridizable therewith; (iv) sequences homologous thereto; (v) sequences encoding similar polypeptides with different colon usage; (vi) altered sequences characterized by mutations, such as deletion, insertion or substitution of one or more nucleotides, either naturally occurring or man induced, either randomly or in a targeted fashion.

According to another aspect of the present invention there is provided a nucleic acid construct comprising the isolated nucleic acid described herein.

According to a preferred embodiment the nucleic acid construct according to this aspect of the present invention further comprising a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as is further detailed hereinunder.

While the isolated nucleic acid described herein is an essential element of the invention, it is modular and can be used in different contexts. The promoter of choice that is used in conjunction with this invention is of secondary importance, and will comprise any suitable promoter sequence. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in E., coli (wherein the construct comprises an appropriate selectable marker and origin of replication) and be compatible for propagation in cells, or integration is the genome, of an organism of choice. The construct according to this aspect of the present invention can be, for example, a plasmid, a bacmid, a phagemid, a cosmid, a phage, a virus or an artificial chromosome.

The present invention has the potential to provide transgenic gene and polymorphic gene animal and cellular (cell lines) models as well as for knock-out and knock-in models. These models may be constructed using standard methods known in the art and as set forth in U.S. Pat. Nos. 5,487.992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194:251–270 1991); Capecchi, Science 244:1288–1292 1989); Davies et al., Nucleic Acids Research, 20 (11) 2693–2698 1992); Dickinson et al., Human Molecular Genetics, 2(8): 1299–1302 1993); Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:7414 750 1991); Jakobovits et al., Nature, 362:255–261 1993); Lamb et al., Nature Genetics, 5: 22–29 1993); Pearson and Choi, Proc. Natl. Acad. Sci. USA 1993). 90:10578–82; Rothstein, Methods in Enzymology, 194:281–301 1991); Schedl et al., Nature, 362: 258–261 1993); Strauss et al., Science, 259;1904–1907 1993). Further, patent applications WO 94/23049, WO93/14200, WO 94/06408, WO 94/28123 also provide information.

All such transgenic gene and polymorphic gene animal and cellular (cell lines) models and knock-out or knock-in models derived from claimed embodiments of the present invention, constitute preferred embodiments of the present invention.

Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a ligand, hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex vivo and (ii) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells an not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronada, Calif.).

These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene W be transferred and only include the specific amino acid coding region.

The expression vehicle can include a promoter for controlling transcription of the heterotogous material and can be either a constitutive or inducible promoter to allow selective transcription. Enhancers that may be requited to obtain necessary transcription levels can optionally be included. Enhancers are generally any nontranslated DNA sequence which works contiguously with the coding sequence (in cis) to change the basal transcription level dictated by the promote. The expression vehicle can also include a selection gene as described hereinbelow.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et at. (Biotechniques 4 (6): 504–512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Features that limit expression to particular cell type can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses ere very specialized infectious agents that have evolved, in may cases, to elude host defense mechanisms. Typically, viruses infect and propagate in specific cell types. The targeting specificity of viral utilizes its natural specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic to be treated then a viral vector is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that arc formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous err subcutaneous injection into the subject. Injection of the viral vectors into a spinal fluid can also be used as a mode of administration. Following injection, the viral vectors will circulate until they recognize best cells with appropriate target specificity for infection.

Thus, according to an alternative embodiment, the nucleic acid construct according to the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stern cells that underwent a homologous recombination event with the construct. Such cells can be introduced into developing embryos to generate chimeras, the offspring thereof can be tested for carrying the knock-out or knock-in constructs. Knock-out and/or knock-in constructs according to the present invention can be used to further investigate the functionality of NRG-4. Such, constructs can also be used in somatic and/or germ cells gene therapy to destroy activity of a defective, gain of function, e.g., dominant, NRG-4 allele or to replace the lack of activity of a silent NRG-4 allele in an organism, thereby to down or upregulate ErbB-4 activity, as required. Further detail relating to the construction and use of knockout and knock-in constructs can be found in Fukushige, S. and Ikeda, J. E.: Trapping of mammalian promoters by Cre-lox site-specific recombination. DNA Res 3 (1996) 73–50; Bedell, M. A., Jerkins, N. A. and Copeland, N. G.: Mouse models of human disease. Part I: Techniques and resources for genetic analysis in mice. Genes and Development 11 (1997) 1–11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751–62, which are incorporated herein by reference.

According to yet another aspect of the present invention there is provided a host cell (either prokaryote or eukatyote) or animal comprising a nucleic acid construct or a portion thereof as described herein. Such a portion may include a coding region and optionally cis acting regulatory sequences. Such a construct or portion may be transient in the cells or organism or be stably integrated in the genome thereof.

According to still another aspect of the present invention there is provided an oligonucleotide of at least 17, at least 18, at least 19, at least 20, at least 22, at least 25, at least 30or at least 40, bases specifically hybridizable with the isolated nucleic acid described herein.

Hybridization of shorter nucleic acids (below 204by in length, e.g., 17–40 bp in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 4.1% nonfat dried milk, hybridization temperature of 1–1.5° C. below the $T_m$, final wash solution of 3 M TMACl, 0.01 M sodium phosphate (pH 6.8), 1 m EDTA (pH 7.6), 0.5% SDS at 1–1.5° C. below the $T_m$, moderate hybridization is effected by a hybridization solution of 6×SSC and 0.1% SDS or 3 M TMACl, 0.01 M sodium phosphate 6.8), 1 mM EDTA(pH 7.6), 0.6% SDS, 100 µg/ml denatured salmon sperm DNA and 0.1% nonfat dried milk, hybridization temperature of 2–2.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each independently of at least 17, at feast 18, at least 19, at least 20, at least 22, at least 25, at least 34 or at least 40 bases specifically hybridizable with the isolated nucleic acid described herein in an opposite orientation so as to direct exponential amplification of a portion thereof, say of 15 to 3000 bp, in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably selected to have comparable melting temperatures (Tm), e.g., melting temperatures which differ by less than that 7° C., preferably less than 5° C., more preferably less than 4° C., most preferably less than 3° C., ideally between 3° C. and zero° C. Consequently, according to yet an additional aspect of the present invention there is provided a nucleic acid amplification product obtained using the pair of primers described herein. Such a nucleic acid amplification product can be isolated by gel electrophoresis or any other size based separation technique Alternatively, such a nucleic acid amplification product can be isolated by affinity separation, either stranded affinity or sequence affinity. In addition, once isolated, such a product cart be further genetically manipulated by restriction, ligation and the like, to serve any one of a plurality of applications associated with up and/or down regulation of NRG-4 activity an further detailed herein.

According to still an additional aspect of the present invention there is provided an antisense oligonucleotide comprising a polynucleotide or a polynucleotide analog of at least 10 bases, preferably between 10 and 15, more preferably between 5 and 20 bases, most preferably, at least 17; at least 18, at least 19, at least 20, at least 22, at least 25, at least 30 or at least 40 bases being hybridizable in vivo, under physiological conditions, with a portion of a polynucleotide strand encoding a polypeptide at least 50%, at least 55% at least 60% at least 65%, at least 70%, at least 75%, at least 80%, at least 85%, at least 90% or more, say at least 96%, at least 92%, at least 93%, at least 94%, at least 95%, at last 96%, at least 97%, at least 98%, at least 99% or 00% homologous (similar+identical acids) to SEQ ID NOs:2 or 15 as determined using the BestFit software of the Wisconsin sequence analysis package, utilizing the Smith and Waterman algorithm, where gap creation penalty equals 8 and gap extension penalty equals 2. Such antisense oligonucleotides can be used to downregulate expression as further detailed hereinunder. Such an antisense oligonucleotide is readily synthesizable using solid phase oligonucleotide synthesis.

The ability of chemically synthesizing olignnucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligouclegotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated. At the translation level, antisense oligonucleotides or analogs that bind target mRNA molecules prevent, by steric hindrance binding of essential translation factors (ribosomes), to the target mRNA a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation (Szczylik et al., 1991), growth (Calabretta et al.; 1941), entry into the S phase of the cell cycle (Heikhila et al., 1987), reduced survival (Reed et al., 1990) and prevent receptor mediated responses (Burch and Mahan,1991).

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are typically impractical for use as antisense sequences since they have short in vivo half-lives, during which they are degraded rapidly by nucleases. Furthermore, they are difficult to prepare in more than milligram quantities. In addition, Such oligonucleotides are poor cell membrane penetraters.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases. thereby improving binding conditions with regard m ionic strength and pH.

In addition, in order to improve half-life as well as membrane penetration, a large number of variations in polynucleotide backbones have been done.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate brides, carboxymethyl ester bridges, carbonate bridges, carboxymethyl ester bridges; acetamide bridges, carbonate bridges, thioether bridges, sulfoxy bridges, sulfono bridges, various "plastic" DNAs, α-anomeric bridges and borane derivatives.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking or ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—).

International patent application WO 92/20702 describe an acyclic oligonucleotide which includes a peptide backbone on which any selected chemical nucleobases or analogs are stringed and serve an coding characters as they do in natural DNA or RNA. These new compounds, known as peptide nucleic acids (PNAs), are not only more stable in cells than their natural counterparts, but also bind natural DNA and RNA, 50 to 100 times more tightly than the natural nucleic acids cling to each other. PNA oligomers can be synthesized from the four protected monomers containing thymine, cytosine, adenine and guanine by Merrifteld solid-phase peptide synthesis. In order to increase solubility in water and to prevent aggregation, a lysine amide group is placed at the C-terminal region.

Thus, in one preferred aspect antisense technology requires pairing of messenger RNA wish an oligonucleotide to form a double helix that inhibits translation. The concept of antisense-mediated gone therapy was already introduced in 1978 for cancer therapy. This approach was based on certain genes that are crucial in cell division and growth of cancer cell. Synthetic fragments of genetic substance DNA can achieve this goal. Such molecules bind to the targeted gene molecules in RNA of tumor cells, thereby inhibiting the translation of the gates and resulting in dysfunctional growth of these cells. Other mechanisms has also been proposed. These strategies have been used, with some success is treatment of cancers, as well or other illnesses, including viral and other infectious diseases. Antisense oligonucleotides are typically synthesized in lengths of 13–30 nucleotides. The life span of oligonucleotide molecules in blood is rather shots. Thus, they have to be chemically modified to prevent destruction by ubiquitous nucleases present in the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dozens of other nucleotide analogs have also been tested in antisense technology.

RNA oligonucleotides tray also be used for antisense inhibition as they form a stable RNA—RNA duplex with the target, suggesting efficient inhibition However, due to their low stability RNA oligonucleotides are typically expressed inside the cells using vectors designed for this purpose. This approach is favored when attempting to target a mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carries. The pharmaceutically acceptable carrier can be, for example, a liposome loaded with the antisense oligonucleotide. Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include but ate not limited to, sterile aqueous solutions which tray also contain buffers, diluents and other suitable additives.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest. The possibility of designing ribozymes to cleave any specific target RNA has rendered them valuable toots in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation Several ribozymes are in various stages of clinical trials. ANGIOZYME was the first chemically synthesized ribozyme to be studied in human clinical orals. ANGIOZYME specifically inhibits formation of VEGF-r (Vascular Endothelial Growth Factor receptor), a key component in the angiogenesis pathway, Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated-WEB home page).

According to yet a further aspect of the present invention there is provided a recombinant or synthetic (i.e., prepared using solid phase peptide synthesis) protein comprising a polypeptide capable of binding is ErbB-4 receptor and which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID Nos: 2 or 15 as determined using the BestFit software of the Wisconsin sequence analysis package, utilizing the Smith and Waterman algorithm, where gap creation penalty equals 8 and gap extension penalty equals 2.

Most preferably the polypeptide includes at least a portion of SEQ ID NO:2 or 15. That portion may include amino acids at position position 4 to position 50 which include the EGF-like domain of NRG-4.

Additionally or alternatively, the polypeptide according to this aspect of the present invention is preferably encoded by a polynucleotide hybridizable with SEQ ID NOs: 1 or 14 or a portion thereof under any of the stringent or moderate hybridization conditions described above for long nucleic acids. Still additionally or alternatively, the polypeptide according to this aspect of the present invention is preferably encoded by a polynucleotide at least 50%, at least 55% at least 60% at least 65% at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 or portions thereof as determined using the BestFit software of the Wisconsin sequence analysis package, utilizing the Smith and Waterman algorithm, where gap weight equals 50, length weight equals 3, average match equals 10 and average mismatch equals −9.

Thus, this aspect of the present invention encompasses (i) polypeptides as set forth in SEQ ID NOs:2 or 15; (ii) fragments thereof; (iii) polypeptides homologous thereto; and (iv) altered polypeptide characterized by mutations, such as deletion, insertion or substitution of one or more amino acids, either naturally occurring or man induced, either random or in a targeted fashion, either natural, non-natural or modified at or after synthesis.

According to still a further aspect of the present invention there is provided a pharmaceutical composition comprising, as an active ingredient the recombinant protein described herein and a pharmaceutical acceptable carrier which is further described above.

According to another aspect of the present invention there is provided a peptide or a peptide analog comprising a stretch of at least 6, at least 7, at least 8, at least 9, at least 10, 10–15, 12–17, or 15–20 consecutive amino acids or analogs thereof derived from a polypeptide at least 50% at least 55% at least 60% at lease 65% at least 70%, at least 75%, at least 80%., at least 85%, at least 90% or more, say at least 91%, at least 92, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the peptide or the peptide analog according to this aspect of the present invention comprises a stretch of at least 6, at least 7, at least 8, at least 9, at least 10, 10–15,12–17, or 15–20 consecutive amino acids or analogs thereof derived from SEQ ID NOs:2 or 15.

As used herein in the specification and in the claims section below the phrase "derived from a polypeptide" refers to peptides derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

As used herein in the specification and in the claims section below the term "amino acid" is understood to include the 20 naturally occurring amino acids; those amino acids often modified post-translationally in vivo, including for example hydroxyproline, phosphoserine and phospho-threonine; and other unusual amino acids including, but not limited to, 2-aminoadipic acid: hydroxylysine isodesmosine, nor-valine, nor-leucine and omithine. Furthermore, the term "amino acid" includes both D- and L-amino acids, Further elaboration of the possible amino acids usable according to the present invention and examples of non-natural amino acids are given hereinunder.

Hydrophilic aliphatic natural amino acids can be substituted by synthetic amino acids, preferably Nleu, Nval and/or α-aminobutyric acid or by aliphatic amino acids of the general formula—$HN(CH_2)_nCOOH$, wherein n=3–5, as well as by branched derivatives thereof, such as, but not limited to:

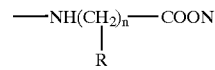

wherein R is, for example, methyl, ethyl or propyl, located at any one or more of the n carbons.

Each one, or more, of the amino acids can include a D-isomer thereof. Positively charged aliphatic carboxylic acids, such as, but not limited to, $H_2N(CH_2)_nCOOH$, wherein n=2–4 and $H_2N—C(NH)—NH(CH_2)_nCOOH$, wherein n=2–3, as well as by hydroxy Lysine, N-methyl Lysine or omithine (Orn) can also be employed. Additionally, enlarged aromatic residues, such as, but not limited to, $H_2N—(C_6H_6)—CH_2—COOH$, p-aminophenyl alanine, $H_2N—F(NH)—NH—(C_6H_6)—CH_2—COOH$, p-guanidinophenyl alanine or pyridinoalanine (Pal) can also be employed. Side chains of amino acid derivatives (if these are Ser, Tyr, Lys, Cys or Orn) can be protected-attached to alkyl, aryl, alkyloyl or aryloyl moieties. Cyclic derivatives of amino acids can also be used. Cyclization can be obtained through amide bond formation, e.g., by incorporating Glu, Asp, Lys, Orn, di-amino butyric (Dab) acid, di-aminopropionic (Dap) acid at various positions is the chain (—CO—NH or —NH—CO bonds). Backbone to backbone cyclization can also be obtained through incorporation of modified amino acids of the formulas H—$N((CH_2)_n—COOH)—C(R)H—COOH$ or H—$N((CH_2)_n—COON)—C(R)H—NH_2$, wherein n=1–4, and further wherein R is any natural or non-natural side chain of an amino acid. Cyclization via formation of S—S bonds through incorporation of two Cys residues is also possible. Additional side-chain to side chain cyclization can be obtained via formation of an interaction bond of the formula —(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap, Peptide bonds (—CO—NH—) within the peptide may be substituted by N-methylated bonds (—$N(CH_3)$—CO—), ester bonds (—C(R)H—C—O——O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom. These modifications can occur at any of the bonds along the peptide chain and even at several (2–3) at the same time. Natural aromatic amino acids, Trp, Tyr and Phe, may be substituted far synthetic port-natural acid such as TIC, naphthylelanine (Nol), ring-methylated derivatives of Phe, halogenated derivatives of Phe or o-methyl Tyr.

According to still another aspect of the present invention there is provided a display library comprising a plurality of display vehicles (such as phages, viruses or bacteria) each displaying at least 6, at least 7, at least 8, at least 9, at least 10, 10–15, 12–17, or 15–20 consecutive amino acids derived from a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, when gap creation penalty equals 8 and gap extension penalty equals 2.

According to a preferred embodiment of this aspect of the present invention substantially every 6, 7, 8, 9, 10, 10–15, 12–17 or 15–20 consecutive amino acids derived from the polypeptide which is at least 50%, at least 55% at least 60% at least 65%, at least 70%, at least 75%, at least 80%, at least 85%, at least 90% or more, say at least 91%, at least 92%, at least 93, at least 94%, at least 95%, at least 96%, at least 97%, at least 98%, at least 99% or 100% identical or homologous (identical+similar) to SEQ ID NOs:2 or 15 are displayed by at least one at the plurality of display vehicles, so as to provide a highly representative library. Preferably, the consecutive amino acids or amino acid analogs of the peptide or peptide analog according to this aspect of the present invention are derived from SEQ ID NOs.2 or 15.

Methods of constructing display libraries are well known in the art, such methods are described, for example, in Young A C, et al., "The three-dimensional structures of a polysaccharide binding antibody to Cryptococcus neoformans and its complex with a peptide from a phage display library: implications for the identification of peptide mimotopes" J Mol Biol Dec 12, 1997;274(4):622–34; Giebel L B et al. "Screening of cyclic peptide phage libraries identifies ligands that bind streptavidin with high affinities" Biochemistry Nov 28, 1995;34 (47):15430–5; Davies E L et al., "Selection of specific phage-display antibodies using libraries derived from chicken immunoglobulin genes" J Immunol Methods Oct. 12, 1995;186(1):125–35; Jones C et al. "Current trends in molecular recognition and bioseparation" J Chromatogr A Jul 14, 1995;707(1):3–22; Deng S J et al. "Basis for selection of improved carbohydrate-binding single-chain antibodies from synthetic gene libraries" Proc Natl Acad Sci U S A May 23, 1995;92(11):4992–6; and Deng S J et al. "Selection of antibody single-chain variable fragments with improved carbohydrate bidding by phage display" J Biol Chem Apr 1, 1994;269(13):9533–8, which are incorporated herein by reference. Display libraries according to this aspect of the present invention can be used to identify and isolate polypeptides which are capable of up- or down-regulating ErbB-4 activity.

According to still another aspect of the present invention then is provided an antibody comprising an immunoglobulin specifically recognizing and binding a polypeptide at least 50%, at least 65% at least 60% at least 65%, at least 70%, at least 75%, at last 80%, at least 85%, at least 90% or more, say at least 91%, at least 92%, at last 93%, at least 94%: at least 95%, at last 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention the antibody specifically recognizing and binding the polypeptides set forth in SEQ ID NOs:2 or 15.

The present invention can utilize serum immunoglobulins, polyclonal antibodies or fragments thereof, (i.e., immunoreactive derivative of an antibody), or monoclonal antibodies or fragments thereof. Monoclonal antibodies of purified fragments of the monoclonal antibodies having at least a portion of an antigen bidding region, including such as Fv, F(abl)2, Fab fragments (Harlow and Lane, 1988 Antibody, Cold Spring Harbor); single chain antibodies (U.S. Pat. No. 4,946,778), chimeric or humanized antibodies and complementarily determining regions (CDR) may be prepared by conventional procedures. Purification of these serum immunoglobulins antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104–126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies are well known in the art, as summarized for example in reviews such as Tramontano and Schloeder, Methods in Enzymology 178, 551–568, 1989. A recombinant or synthetic NRG-4 or a portion thereof of the present invention may be used to generate antibodies in vitro. More preferably, the recombinant or synthetic NRG-4 of the present invention is used to elicit antibodies in vivo. In general, a suitable host animal is immunized with the recombinant or synthetic NRG-4 of the present invention or a portion thereof including at least one continuous or discontinuous epitope. Advantageously, the animal host used is a mouse of an inbred strain. Animals are typically immunized with a mixture comprising a solution of the recombinant or synthetic NRG-4 of the present invention or portion thereof in a physiologically acceptable vehicle, and any suitable adjuvant, which achieves as enhanced immune response to the immunogen. By way of example, the primary immunization conveniently may be accomplished with a mixture of a solution of the recombinant or synthetic NRG-4 of the present invention or a portion thereof and Freund's complete adjuvant, said mixture being prepared in the form of a water-in-oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding can be determined during the immunization schedule by any convenient method including by way of example radioimmunoassay, or enzyme linked immunosorbant assay, which is known as the ELISA assay. When suitable antibody titers are achieved, antibody producing lymphocytes from the immunized animals are obtained, and these are cultured, selected and closed, as is known in the art. Typically, lymphocytes may be obtained in large numbers from the spleens of immunized animals, but they may also be retrieved from the circulation, the lymph nodes or other lymphoid organs. Lymphocyte are then fused with any suitable myeloma cell line, to yield hybridomas, as is well known in the art. Alternatively, lymphocytes may also be stimulated to grow in culture; and may be immortalized by methods known in the art including the exposure of these lymphocytes to a virus; a chemical or a nucleic acid such as an oncogene, according to established protocols. After fusion, the hybridomas ate cultured under suitable culture conditions, for example in multiwell plates, and the culture supernatants are screened to identify cultures containing antibodies that recognize the hapten of choice. Hybridomas that secrete antibodies that recognize the recombinant or synthetic NRG-4 of the present invention are cloned by limiting dilution and expanded, under appropriate culture conditions. Monoclonal antibodies are purified and characterized in terms of immunoglobulin type and binding affinity.

The following embodiments of the present invention are directed at intervention with NRG-4 activity and therefore with ErbB-4 receptor signaling.

Thus, according to yet another aspect of the present invention there is provided a pharmaceutical composition comprising, as an active ingredient, an agent for regulating an endogenous protein affecting ErbB-4 receptor activity in vivo or in vitro, the endogenous protein being at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein affecting ErbB-4 receptor activity in vivo or in vitro. The method according to this aspect of the present invention is effected by administering an agent for regulating the endogenous protein activity in vivo, the endogenous protein being at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

An agent which can be used according to the present invention to upregulate the activity of the endogenous protein can include, for example, an expressible sense polynucleotide at least 50%, at least 55% at least 60% at least 65% at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to upregulate the activity of the endogenous protein can include, for example, at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

An agent which can be used according to the present invention to downregulate the activity of the endogenous protein can include, for example, an expressible antisense polynucleotide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to downregulate the activity of the endogenous protein can include, for example, an antisense oligonucleotide or ribozyme which includes a polynucleotide or a polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases which is hybridizable in vivo, under physiological conditions, with a portion of a polynucleotide strand encoding a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

Still alternatively, an agent which can be used according to the present invention to downregulate the activity of the endogenous protein can include, for example, an peptide or a peptide analog representing a stretch of at least 6, at least 7, at least 8, at least 9, at least 10, 10–15, 12–17, or 15–20 consecutive amino acids or analogs thereof derived from a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

Peptides or peptide analogs containing the interacting EGF-like domain of NRG-4 according to the present invention will compete by protein interactions to form protein complexes with ErbB-4, inhibiting or accelerating the pathways in which ErbB-4 is involved.

The following biochemical and molecular systems are known for the characterization and identification of protein-protein interaction and peptides as substrates, through peptide analysis, which systems can be used to identify inhibitory peptide sequences. One such system employs introduction of a genetic material encoding a functional protein or a mutated form of the protein, including amino acid deletions and substitutions, into cells. This system can be used to identify functional domains of the protein by the analysis of its activity and the activity of its derived mutants in the cells. Another such system employs the introduction of small encoding fragments of a gene into cells, e.g., by means of a display library or a directional randomly primed cDNA library comprising fragments of the gene, and analyzing the activity of the endogenous protein in their presence (see, for example, Gudkov et al. (1993) "Isolation of genetic suppressor elements, including resistance to topoisomerase II interactive cytotoxic drugs, from human topoisomerase II cDNA" Proc. Natl. Acad. Sci. USA 90:3231–3236; Gudkov and Robinson (1997) "Isolation of genetic suppressor elements (GSEs) from random fragment cDNA libraries in retroviral vectors" Methods Mol Biol 69;221–240; and Pestov et al. (1999) "Flow Cytometric Analysis of the cell cycle in transfected cells without cell fixation" Bio Techniques 26:102–106). Yet an additional system is realized by screening expression libraries with peptide domains, as exemplified, for example, by Yamabhai et al. (1998 "Intersectin, a Novel Adaptor Protein with Two Eps15 Homology and Five Src Homology 3 Domains". J Biol Chem 273: 31401–31407). In yet another such system overlapping synthetic peptides derived from specific gene products are used to study and affect in vivo and in vitro protein-protein interactions. For example, synthetic overlapping peptides derived from the HIV-1 gene (20–30 amino acids) were assayed for different viral activities (Baraz et al. (1998) "Human immunodeficiency virus type 1 Vif derived peptides inhibit the viral protease and arrest virus production" FEBS Letters 441:419–426) and were found to inhibit purified viral protease activity; bind to the viral protease; inhibit the Gag-Pol polyprotein cleavage; and inhibit mature virus production in human cells.

The Her/ErbB tyrosine kinase growth factor receptor family is presently known to includes four plasma membrane-spanning receptors, ErbB-1 (also known as the Epidermal Growth Factor Receptor), ErbB-2, ErbB-3 and ErbB-4. These receptor tyrosine kinases are typically activated in a ligand-dependent manner, resulting in receptor oligomerization, their self-phosphorylation upon key intracellular tyrosine residues and subsequent activation of downstream signaling cascades. ErbB receptors and their corresponding ligands play numerous instrumental roles in mammalian development and have also been demonstrated to act as potent oncogenes in for example, breast cancer (ErbB1 and ErbB2) and in glioblastoma (ErbB1). Overexpression of different ErbBs in many other cancers, often correlating with poorer survival prognosis, implicates a far greater functional role of ErbBs and their ligands in oncogenesis (reviewed in: Burden and Yarden., 1997; Klapper et al 2000).

For a particular cell type, ErbB signaling is dependent upon two major factors (i) the quantity and type of ErbB receptors that the cell expresses; and (ii) the quantity and type of ligands that activate cells expressing ErbB receptors.

Upon activation, each ErbB receptor has the capacity to recruit different intracellular substrates, thus allowing alternative signaling cascades to be activated. Ligand-induced formation of inter-ErbB heterodimers (e.g., ErbB2–ErbB4 oligomers) often takes place in preference to ErbB homodimers (e.g., ErbB4—ErbB4 oligomers). Heterodimerization is an important process in ErbB signaling. For example, the highly active and oncopotent ErbB2 receptor to date has no known ligand that directly binds it, although it can be activated in trans through its binding to other ErbB receptors (Tzahar et al., 1997 and 1998).

Typically, ErbBs are activated in a ligand-dependent manner. Cells expressing a particular repertoire of ErbB receptors can be activated in a different manner, depending on the incident ErbB ligands that bind them. For example the ErbB-ligand Epidermal Growth Factor (EGF), strongly activates ErbB1 homodimers, with activating ErbB4 under normal physiological conditions (Tzahar et al, 1996). In contrast Neuregulin-4 (NRG-4), the subject of the present invention, strongly activates ErbB2–ErbB4 heterodimers, weakly activates ErbB4—ErbB4 homodimers and does not activate ErbB1 homodimers. Thus in a scenario where a particular cell expresses ErbB1, ErbB2 and ErbB4, activation by EGF or by NRG-4 can result in very different responses, as different components of the ErbB signaling network are recruited.

The present invention describes the first characterization of NRG-4, a novel member of the ErbB ligand family, whose structure, expression pattern and restrained receptor-binding properties suggest a unique physiological role. Gene-targeting and in vitro studies with recombinant NRG-4 may resolve the presumed distinct biological role of this growth factor and its relationship to other EGF/NRG family ligands. Thus, the present invention exemplifies:

First, the discovery of the first cDNA variant of mouse NRG-4, including the region encoding the EGF-like domain, essential for ErbB-binding.

Second, the isolation and characterization of mouse genomic DNA, which harbors two exons found in the aforementioned mouse cDNA; one of these exons which encodes the invariant amino-terminus of the EGF-like domain. The intron-exon boundary for one of these exons is identical to that found for the prototypical NRG-1 gene, indicating that the two genes are ancestrally related. Should NRG-4 indeed follow the example of the prototypical NRG-1 gene, then another isoform of the EGF-like domain may still exist, with an alternatively encoded COOH-terminus.

Third, the isolation of the human NRG-4 cDNA gene, highly homologous to the mouse sequence.

Fourth, characterization of NRG-4 binding to ErbB receptors. Numerous strategies were employed to demonstrate that NRG-4 directly binds to the ErbB4 receptor, and preferably activates through ErbB4–ErbB2 heterodimers.

Fifth, the generation and characterization of neutralizing NRG-4 antibodies as a pharmacological tool to block NRG-4 binding through its EGF-like domain.

Sixth, the expression profile of NRG-4, implicating a natural role of this ligand in muscles, the pancreas these finding serving as a spring-board to test natural physiological roles of this ligand that may be of therapeutic benefit.

The very specific and unusually restricted binding profile of NRG-4 may be exploited for both pharmacological and diagnostic purposes Traceable synthetic/recombinant NRG-4-tagged molecules can serve as a diagnostic tool in which cells binding NRG-4 can be measured. For example, the oncogenic ErbB2 receptor serves as a marker in breast cancer patients that predicts low chances of remission after standard chemotherapy protocol. However, numerous studies implicate the requirement of ErbB2 to be co-activated along with other ErbBs. Thus, the stratification of sub-groups of breast cancer patients co-overexpressing ErbB2 with different ErbBs is less well defined. A traceable NRG-4-tagged molecule would serve as a sensitive physiological tool to elucidate if these ErbB2 overexpressors also co-overexpress ErbB4.

The extremely limited but specific ErbB-binding profile of NRG-4 can be exploited in the generation of NRG-4-tagged molecules that can specifically target bound drugs to cells with affinity to NRG-4. Of the known ErbB receptors it is shown herein that the EGF-like domain of NRG-4 can only bind with high affinity to cells co-expressing ErbB4 and ErbB2 and perhaps in a lesser extent to cells co-expressing ErbB1 and ErbB4. This extremely limited binding profile can allow the delivery of drugs to a limited repertoire of cells, allowing for smaller drug doses to be used and limiting the chances of generic toxic side effects to take place in patients. For example, patients displaying cancers co-overexpressing ErbB4 and ErbB2 may benefit from a NRG-4-tagged drug delivery vehicle.

The extremely limited but specific ErbB-binding profile of NRG-4 can also be exploited to activate a small repertoire of cells that express high affinity receptors that can be activated by it. Expression of NRG-4 in adult pancreatic and muscle cells indicate that NRG-4 can modulate distinct physiological processes, both in development as well as in the adult. The high conservation between human and mouse NRG-4, particularly within the EGF-encoding domain further implicate an important role of NRG-4 in mammals. These bioactivities may be further exploited for biopharmaceutical purposes.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animals Cells—A Manual of Basic Technique" by Freshney, Wiley-Liss, N. Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986), "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Materials:

EGF (human, recombinant) was purchased from Boehringer Mannheim. Recombinant human NDFβ1$_{177-246}$ (NRG-1-β1) was obtained from Amgen (Thousand Oaks, Calif.). Iodogen and bis(sulfosuccinimidyl) suberate (BS$^3$) were from Pierce. Monoclonal antibodies (mAbs) to ErbB proteins (Chen et al., 1996; Klapper et al., 1997) were used for immunoprecipitation. The composition of buffered solutions was described (Tzahar et al., 1994). Recombinant soluble extracellular domains of the four ErbB proteins (denoted IgB-1 through 4) (Chen et al., 1996), in the form of fusion proteins containing the Fc portion of human immmunoglobulin G (IgG) were harvested from serum-free conditioned media of transfected HEK-293 human embryonic kidney cells. The PY20 antibody was purchased from Santa Cruz Biotechnology. A mAb to the active form of the MAP kinase (Yung et al., 1997) was a gift from R. Seger (of the Weizmann Institute, Israel).

Peptide synthesis:

The mouse EGF-like domain of NRG-4 (residues 4 to 50, SEQ ID NO:2) was synthesized on an Applied Biosystems (ABI) 430A peptide synthesizer using standard tert-butyloxycarbonyl (t-Boc) chemistry protocols as described (Barbacci et al., 1995). Acetic anhydride capping was employed after each activated ester coupling. The peptide was assembled on phenylacetamidomethyl polystyrene resin using standard side chain protection, except for the use of t-Boc-Glu(O-cyclohexyl) and t-Boc-Asp(O-cyclohexyl). The peptide was deprotected using the "Low-High" hydrofluoric acid (HF) method (Tam et al., 1983). The crude HF product was purified by reverse phase HPLC (C-18 Vydac, 22×250 mm), diluted without drying into folding buffer (1 M urea, 100 mM Tris, pH 8.0, 1.5 mM oxidized glutathione, 0.75 mM reduced glutathione, 10 mM methionine), and stirred for 48 h at 4 C. The folded, fully oxidized peptide was purified from the folding mixture by reverse phase HPLC, and characterized by electrospray mass spectroscopy. A single HPLC peak with an averaged molecular mass (Mr) of 5371.50 was displayed by the reduced peptide prior to folding. This mass is in agreement with the theoretical Mr (5371.20). The folded and oxidized peptide displayed a slightly lower averaged molecular mass of 5366.88.

Database searches:

EST databases were scanned for homology to the EGF-like domain of NRG-1β (NDF-β) by Blast and Smith-Waterman algorithms (Samuel & Altschul, 1990; Smith & Waterman, 1981) using both a Unix-interfaced GCG server and a Bioaccelerator device (Compugen, Israel). Obtained clones (Accession numbers AA238077 (mouse) and AI743118 (human)) were sequenced bi-directionally to both confirm fidelity of published sequences and to extend the sequence of the clones beyond that published in the EST databases. In the case of the human EST clone which contained an apparent insert in the open reading frame, PCR primers were generated in order to pull out a variant without this insert by means of RT-PCR (see below).

Genomic screen:

PCR primers designed to amplify predicted exon-6 of NRG-4 were synthesized and used to screen a P1 genomic library derived from mouse strain 129. A single positive P1 clone was identified, subsequently subcloned by shotgun ligation and identification of Exon-6 positive bluescript integrants. One such vector, harboring a 10 Kb insertion was mapped and partially sequenced revealing Exon-5 and Exon-6 sequences.

RT-PCR:

Total RNA was extracted from T47D and MCF-7 human breast cancer cell lines (TRIZOL Reagent). 5 μg of total RNA was used as a template to derive mRNA derived cDNA, using 500 μg/ml Oligo-(dT)$_{12-18}$ as a primer (Gibco BRL superscript kit; Oligo-dT). Forward 5'-CCTACTCTCTTGACCAAGAATGAAAC-3' (SEQ ID NO:16) and reverse 5'-AATGATTTGGTTCACTTTGACG-3' (SEQ ID NO:17) oligonucleotides were synthesized as primers to amplify NRG-4 from the cDNA libraries, amplifying with Roche Expand™ High Fidelity PCR amplification system, using company's recommended amplification conditions and 68 C. annealing/extension temperature. PCR products were run on a 1% agarose gel. Bands of expected mobility were identified from both T47D and MCF-7 cells, were extracted and subcloned into pGEMT (Promega) before sequencing. The human NRG-4 sequence published represents identical findings from two independent PCR reactions.

Northern Blot:

A Northern blot filter was purchased from Clontech (MTN Blot # 7760-1), each lane containing approximately 2 μg of poly(A)$^+$ purified mRNA from healthy human tissues and run on a denaturing 1.2% formaldehyde/agarose gel. Hybridization to cDNA probes to mouse NRG-4 and human β-actin were performed with "ExpressHyb" (Clontech) using the protocol provided by the manufacturer. Probing with a human amylase cDNA probe was performed by standard techniques. After each hybridization, blots were washed at room temperature for 40 minutes with several changes of low stringency wash solution (2×SSC, 0.05% SDS) and then with at least two changes of high stringency buffer (0.1×SSC, 0.1% SDS) at 50° C. for 40 minutes.

Lysate Preparation for Western Blot Analyses:

For receptor activation studies, derivatives of the 32D cell line were resuspended in phosphate-buffered solution (PBS) and incubated at 22 C. for 15 minutes before adding growth factors and incubating for five minutes at 37 C. Cells were then pelleted and lysed in ice cold solubilization buffer [50 mM Tris-HCl pH 7.5, 150 mM NaCl, 1% Noidet-P-40, 0.5% Na-deoxycholate, 0.1% sodium dodecyl sulfate (SDS), 1.5 mM EDTA, 1.5 mM MgCl$_2$, 2 mM Na-orthovanadate, 1 mM phenylmethylsulfonyl fluoride (PMSF), 10 μg/ml aprotinin and 10 μg/ml leupeptin] and left on ice for 15 minutes. The whole cell extract was then cleared by centrifugation (12, 000×g for 10 minutes at 4 C.), immediately boiled in reducing gel sample buffer, and resolved by 10% SDS PAGE before being transferred onto nitrocellulose. Filters were blocked in TBST buffer (0.02 M Tris-HCl pH 7.5, 0.15 M NaCl, 0.05% Tween-20) containing 1% milk for 40 minutes at 22 C., blotted with primary antibodies in TBST overnight at 4 C., followed by conjugation with a secondary antibody linked to horseradish peroxidase and subsequent detection by chemiluminescence (Amersham Corp.).

Radiolabeling of ligands, covalent crosslinking and ligand displacement analyses:

Growth factors were labeled with Iodogen (Pierce) as described (Karunagaran et al., 1995). Chemical crosslinking to Chinese Hamster Ovary (CHO) cells engineered to express different ErbB combinations have been performed essentially as described (Tzahar et al., 1996). Briefly, radiolabeled ligands (at 100 ng/ml) were incubated for 2 hours with cell monolayers at 4 C. The chemical crosslinking agent BS$^3$ (1 mM) was then added and the cells were further incubated for 45 minutes at 22 C. Mouse antibodies were first coupled to rabbit anti-mouse IgG and to protein A-Sepharose beads, and then they were incubated with cell extracts for 2 hours at 4 C. Immunoprecipitated complexes were than washed three times with ice-cold SBN buffer (1% NP-40; 150 mM NaCl; 10% Glycerol; 1 mM EGTA, in 50 mM Tris-HCl, pH 7.4; 1 ml per wash) prior to heating (5 minutes at 95 C.) in gel sample buffer, resolution by gel electrophoresis, transfer to nitrocellulose and autoradiography. For crosslinking with IgBs, after co-incubation of IgB-containing conditioned media with radiolabeled ligands, complexes were immunoprecipitated directly with Sepharose-protein A beads. For ligand displacement analyses, cell monolayers were washed once with binding buffer, and then incubated for 2 hours at 4 C. with radiolabeled NRG-1β (5 ng/ml) and various concentrations of unlabeled ligands, as indicated. Non-specific binding was determined in the presence of a 100-fold molar excess of the unlabeled ligand. Cells were then washed, lysed in a solution containing 0.1 M NaOH and 0.1% SDS, and radioactivity determined by use of a gamma counter.

Antibody generation and Screening:

Two rabbits (#3919 and #3920) were immunized against the refolded synthetic peptide encoding the mouse NRG-4 EGF-like domain in a protocol of five injections, using 10 μg/rabbit of peptide for each injection along with Freund's complete adjuvant for the first injection and incomplete adjuvant for subsequent injections. Cleared serum was tested for binding to NRG-4 in the following experiment: Serum from the two rabbits as well as pre-immune serum (#3919), a non specific rabbit antiserum (anti-Erk-1 beta; a gift from Dr. Ronny Seger, the Weizmann Institute) and IgB1 conditioned medium were pre-adsorbed onto protein-A sepharose beads for 30 minutes at 4 C. in 1 ml and 10 μl of serum/conditioned medium. Beads were then washed three times in HNTG and then blocked in HNTG+0.1% BSA at 4 C. for 30 minutes. Pellets were spun down and resuspended in 0.2 ml HNTG along with 5 μl of $^{125}$I-radiolabeled EGF or NRG-4, where they were incubated for 2 hours at 4 C., then washed four times in HNTG, boiled in protein sample buffer and resolved by 7.5% SDS PAGE. Gels were dried and signals viewed using a phosphorimager (Fugi).

Cell proliferation assays:

The establishment of a series of interleukin 3 (IL-3)-dependent 32D myeloid cells expressing all combinations of ErbB proteins has been described (Alimandi et al., 1997; Pinkas-Kramarski et al., 1996; Shelly et al., 1998). Cells were maintained in RPMI medium with 10% fetal bovine serum (FBS) and dilute IL 3-containing conditioned medium. Prior to proliferation assays, cells were washed three times in RPMI/FBS and plated ($5 \times 10^5$ cells/ml; 0.1 ml/well) into 96-well flat-bottomed plates with the indicated liconcentrations or with IL-3 (1:1000 dilution of conditioned medium). Cell survival was determined 24 hours later, or after the indicated time intervals, by MTT assay, as previously described (Mosman, 1983). MTT (0.05 mg/ml) was incubated with the analyzed cells for 2 hours at 37 C. Living cells can transform the tetrazolium ring into dark blue formazan crystals, that can be quantified by reading the optical density at 540–630 nm after lysis of the cells with acidic isopropanol.

Experimental Results

Identification of a candidate novel ErbB ligand:

With the assumption that there may still exist novel ErbB-specific ligands it was decided to search for new family members by homology. The recent explosion of DNA sequencing data added to DNA databases, largely resultant from the Human Genome Project initiative, offers scanning of these data for novel transcripts coding ligands with homology to the ErbB-3- and ErbB-4-specific ligand, NRG-1 (NDF). The motif $CX_7CXNGGXCX_{13}CXCX_3YXGXRC$ (SEQ ID NO:18), conserved in most isoforms of NRG-1, was used to scan available new DNA sequences. An expressed sequence tag (EST) clone originating from a mouse liver cDNA library (accession number AA238077) was identified, its sequence encoding an EGF-like domain sharing 32% identity with the NRG-1β isoform (Wen et al., 1992). This clone was obtained and fully sequenced, its presumed translation product encoding a protein of 115 amino acids (FIG. 1a, SEQ ID NOs:1 and 2). Hydropathy analysis using the Kyte-Doolittle algorithm (Kyte & Doolittle, 1982) supports the existence of a transmembrane domain (FIG. 1b) characteristic to most NRG isoforms (Marchionni et al., 1993; Wen et al., 1994). Conspicuously, this protein sequence lacks a hydrophobic amino-terminal stretch, commonly found in signal peptide motifs, important in sequestering proteins to traverse the plasma membrane. Most isoforms of NRG-1 also lack consensus signal peptide sequences, but they carry an apolar N-terminal sequence thought to allow transmembrane orientation of the precursor molecule. The predicted extracellular domain of the precursor protein includes the EGF-like domain, whose primary structure displays the entire structural motifs characteristic to the EGF/NRG family (FIG. 1c). The putative cytoplasmic domain of the precursor protein is relatively short and contains one potential site for N-glycosylation. Two additional sites are located at the probable ectodomain.

Alignment of the EGF-like domains of all known ErbB-specific ligands of mammalian origin indicated that the novel transcript encodes a new member of this family (FIG. 1c). Its characteristic six extracellular cysteine residues and their conserved spacing predict the existence of the three disulfide bridges, denoted as A, B and C, that are the landmark of all EGF-like peptides. Besides the six conserved cysteine residues, the new EGF-like domain shares very high homology with other members of the NRG family, including a glycine at position 21 (Gly-21), Gly-42 and Arg-44, along with many semi-conserved residues. Of note, the expected B loop of the protein, like the loops of EGF and NRG-2, is shorter by three residues. Except for the EGF-like domain and the transmembrane topology of the novel predicted protein, it shares no significant sequence homology or structural motifs with other ErbB ligands.

EST-derived clones on occasion can be prone to sequence artifacts. The EGF-encoding domains of ErbB-ligands can alone elicit ErbB-binding. It was, therefor, decided to examine in more detail sequences encoding in particular the EGF-encoding domain of this putative novel ligand, in the very least to confirm the identity of this domain. Two alternative strategies were employed to test this.

The first, was to isolate the genomic locus of the novel ligand, using a probe encoding the EGF-like domain. A P1 clone derived from a mouse strain 129 genomic library was isolated, from which plasmid sub-clones of the P1 vector were generated by shotgun ligation; these fragments being once again screened by hybridization for the EGF-like domain encoding probe. The largest of these sub-clones was characterized more fully. A detailed restriction map was generated and the clone was partly sequenced (FIG. 1d). Two exons were identified, the latter encoding the 5' component of the EGF-like domain and was arbitrarily designated as Exon-6, corresponding to Exon-6 of the prototypical NRG-1 genomic locus. Exons 5 and 6 share 100% sequence identity with the corresponding sequenced mouse EST-cDNA, confirming the quality of the EST clone. Significantly, the intron-exon boundaries of Exon 6 for both NRG-1 and the novel gene are identical, supporting that these genes are derived from a common ancestor, and indicates that the novel ligand is encoded by a new variant of the Neuregulin gene family. As this data supports that the novel ErbB-ligand is a Neuregulin, it was named Neuregulin-4 (NRG-4).

Second, by method of RT-PCR, a human NRG-4 homologue was isolated and sequenced (FIG. 1e). Human primers were initially derived from a second EST clone AI743118, which shares, in part, identical sequence to the reverse transcribed and subcloned human derived NRG-4 isoform presented herein, but also an insertion that disrupts the encoded EGF-domain sequence.

Using the oligonucleotides as RT-PCT primers as described, 10 RT-PCR products were subcloned from MCF7 and T47D cells. Eight of the ten PCR products harbored inserts within the EGF-encoding domain, resulting in disruption of the EGF domain and in all cases, truncation of the predicted amino-acid sequences with the co-current loss of a transmembrane binding motif. A similar insertion was found in the EST clone # AI743118. The functional relevance, if any, of these optionally alternatively spliced isoforms. Should they indeed represent mature mRNA, the predicted protein products would not activate ErbB receptors. It is hypothesize that these transcripts are either partially processed RNAs or if not, may encode proteins that would inhibit ErbB binding.

The predicted translation products for human and mouse NRG-4 share 78% overall identity and 91% identity within the EGF-like encoding domain. All of the differences in the EGF-like domain were encoded entirely by Exon 6, with exact matching amino acid sequences at the COOH terminal. This conserved primary structure demonstrates that these two genes encode the same isoform of the NRG-4 EGF-like domain for both species. Should an other isoform of the EGF-like domain exist for NRG-4 as does for NRG-1, remains to be resolved. The tightly conserved primary structure particularly of the EGF-like domain between mouse and human NRG-4 also demonstrates that selective evolutionary pressure has maintained the integrity of this locus, supportive that this gene plays essential(s) role in mammalian development and/or maintenance.

Figure 2:
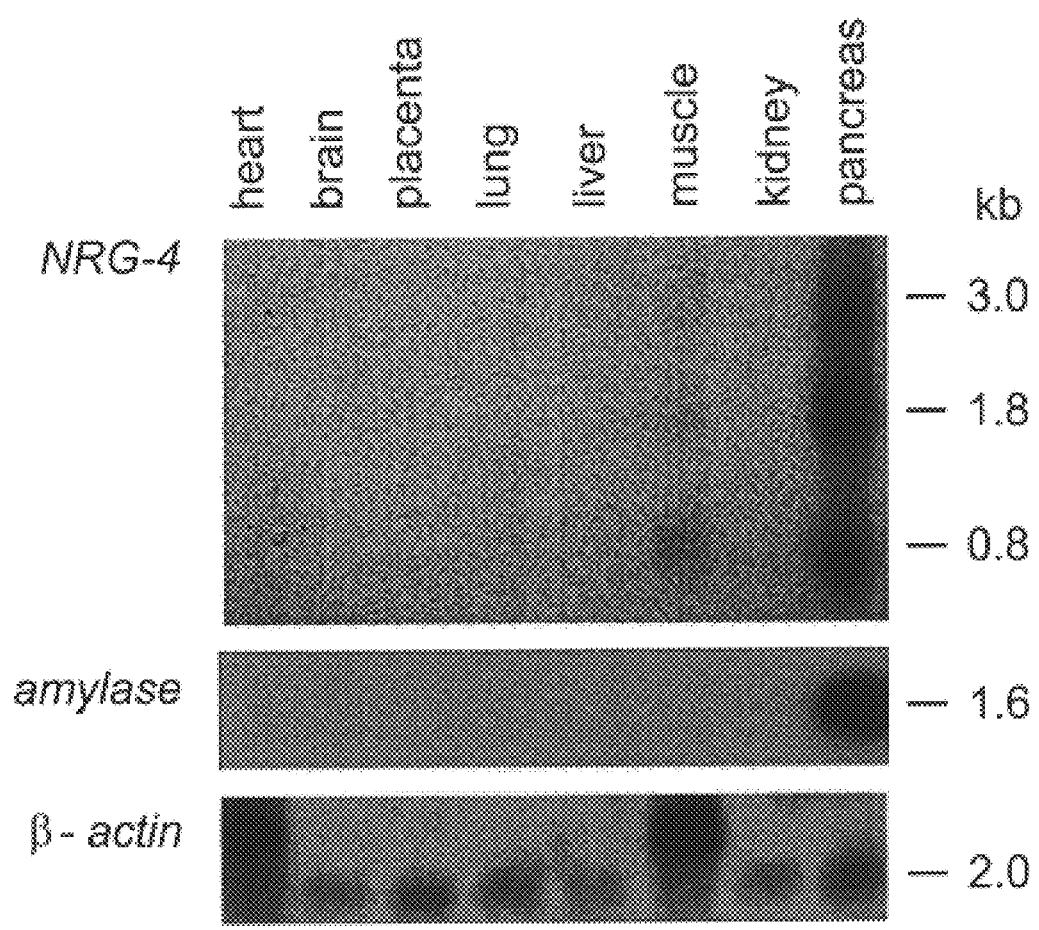
FIG. 2 shows a northern blot analysis of NRG-4 expression in human tissues. Poly(A)-containing RNA from the indicated human tissues (2 μg per lane) was analyzed using a nitrocellulose filter purchased from Clontech (San Diego, Calif.). The blot was hybridized with a full-length mouse NRG-4 cDNA probe radiolabeled using the Klenow fragment of DNA polymerase 1 and random hexamers as primers. Following autoradiography, the filter was stripped of radioactivity and re-probed sequentially with pancreas and muscle markers, alpha-amylase-2 and beta-actin, respectively. Molecular weights of marker molecules are indicated in kilobases (kb). Note that beta-actin probe also hybridized with a larger molecular weight isoform present in heart and in skeletal muscle.

Tissue-specific expression of the novel transcript:

Expression analysis was performed to help elucidate the possible target sites of NRG-4 activity. Northern blot analysis of mRNA isolated from different human adult tissues revealed moderate expression of the NRG-4 transcript in skeletal muscle and high levels in the pancreas (FIG. 2). Other tissues, including brain and placenta, two rich sources of many different growth factors, displayed very low expression, if any. Three discernible molecular weight species (0.8, 1.8 and 3.0 kilobases) were detectable in pancreas and in muscle, indicating the existence of several mRNA isoforms, the smallest band consistent in size with the NRG-4 clone described in this study.

The EGF-like domain of NRG-4 stimulates proliferation of ErbB-4-expressing cells:

To test the prediction that the novel transcript encodes an ErbB-specific ligand, the corresponding full-length EGF-like domain (residues 4–50, FIG. 1a, SEQ ID NO:2) was synthesized, denatured and refolded to allow proper disulfide bridging. This method has been used before to synthesize functionally active derivatives of other EGF-like growth factors (Barbacci et al., 1995; Lin et al., 1988; Shelly et al., 1998). A series of derivatives of the 32D cell line engineered to express different ErbB receptors or their combinations has been previously described (Pinkas-Kramarski et al., 1996; Shelly et al., 1998). The myeloid 32D parental cells require cytokine stimulation, such as interleukin 3 (IL3) for their growth, and were chosen because they lack endogenous ErbB expression. Signaling through different ErbB-receptors can replace the IL3-dependent mitogenicity and survival for these cell lines, and hence this system provides a sensitive means to detect ligand-induced growth signals, which are conveniently measured as a function of cellular metabolic activity by using the [3-(4,5-dimethylthiazol-2-yl)-2,5-diphenyl]tetrazolium bromide (MTT) assay (Mosman, 1983).

Cells singly expressing ErbB-1, ErbB-2 or ErbB-3 (denoted D1, D2 or D3, respectively) did not respond to the synthetic novel peptide in a 24-hour dose-response assay, although responses to EGF (D1 cells), an ErbB-2-stimulatory monoclonal antibody [D2 cells, (Klapper et al., 1997)], or IL-3 (D3 cells) were retained (FIG. 3A, and data not shown). The latter cell line is not responsive to NRGs due to the defective kinase of ErbB-3. However, ErbB-4 expressing cells (D4), exhibited a modest dose-dependent mitogenic response in comparison to its counterpart NRG-1β control. Because different heterodimeric complexes of ErbB proteins can diversify and enhance signaling by EGF-like ligands (Cohen et al., 1996; Pinkas-Kramarski et al., 1996; Riese et al., 1995), cells co-expressing two ErbB protein (for example D12 cells co-express ErbB-1 and ErbB-2) were also tested for NRG-4-induced mitogenicity. Of the tested combinations, namely: D12, D13, D23 and D24 cells, a cell line expressing a combination of ErbB-4 with ErbB-2 (D24 cells) was the only line that responded mitogenically to the novel peptide (FIG. 3A). Notably, co-overexpression of ErbB-1 and ErbB-2 resulted in a relatively high basal proliferation activity, but these cells still responded to EGF (FIG. 3B). Additionally, in cells co-overexpressing ErbB-2 and ErbB-4, NRG-1 and the novel ligand were almost equipotent (compare D4 and D24 panels in FIG. 3A), indicating that ErbB-2 can enhance the mitogenic effect of the novel ligand, as it does for other ErbB ligands (Graus-Porta et al., 1995; Karunagaran et al., 1996; Wang et al., 1998).

A long-term cell survival assay confirmed the ability of the novel growth factor to stimulate ErbB-4. This assay examined the ability of added growth factors to sustain survival of certain 32D derivatives in the absence of IL-3. As in the dose-response experiments, the novel synthetic peptide only stimulated the survival of the two ErbB-4-expressing cell lines we examined, namely D4 and D24 cells (FIG. 3b). Also similar to the short-term dose response assay, stimulation of D24 cells was more robust, and akin to the NRG-1-treated controls than was the response of D4 cells. These data indicate that the NRG-4 growth factor can exert a weak proliferative signal through ErbB-4 alone, but co-expression of ErbB-2 with ErbB-4 allows a superior mitogenic response, as it does in the case of NRG-1 (Wang et al., 1998). On the basis of the ability of the NRG-4 derived synthetic peptide to mediate a biological effect through one of the Neuregulin receptors, this data further supports that it is a Neuregulin, namely Neuregulin-4 (NRG-4).

NRG-4 recognizes and activates ErbB-4:

To elucidate the molecular interactions pertaining to NRG-4 signaling, several different approaches were employed to test specific binding of this growth factor to the four ErbB proteins.

In the first assay, binding studies in a cell-free system were performed with recombinant soluble forms of all four ErbB proteins. The soluble proteins, denoted IgB-1 through 4, consist of a dimeric fusion between the extracellular domain of the corresponding ErbB and the Fc portion of a human immunoglobulin G (Chen et al., 1996). NRG-4, EGF and NRG-1β were radiolabeled with $^{125}$I, incubated with the soluble receptors, and then irreversibly bound to the IgBs using the $BS^3$ covalent crosslinking reagent.

As expected for the controls, a strong signal was detected for EGF binding to IgB-1 in contrast to NRG-1β, which bound strongly to IgB-3 and IgB-4, but no ligand bound to IgB-2 (FIG. 4a). In comparison to NRG-1, $^{125}$I-NRG-4 bound to the soluble form of ErbB-4 (IgB-4) only weakly, with low or no binding to the other IgB proteins (FIG. 4a).

To confirm specificity of the covalent crosslinking assay unlabeled NRG-4 was co-incubated, at 100-fold molar excess, with the radioactive ligand and efficient displacement from IgB-4 was observed (lower panel of FIG. 4a). Thus, consistent with the ability of NRG-4 to induce growth and survival of ErbB-4-expressing cells, but not cells singly expressing the other three ErbB receptors, this ligand recognized only ErbB-4 (IgB4) in solution.

To test the prediction that NRG-4 can recognize a surface-expressed ErbB-4, but no other membrane-bound ErbB protein, a Chinese Hamster Ovary (CHO) cell line was employed. These cells express low amounts of ErbB-2, but no other ErbB receptor, and accordingly failed to bind NRG-4 or any other Neuregulin [(Tzahar et al., 1996) and data not shown]. CHO cells were transfected with plasmid vectors directing expression of ErbB-4, or co-transfected with an ErbB-4 plasmid together with vectors expressing one of the three other ErbB proteins. Two days later, cells were incubated with $^{125}$I-NRG-4, or with a radiolabeled NRG-1 as control, and subsequently the formed ligand-receptor complexes were stabilized by using a covalent crosslinking reagent. Immunoprecipitation of the expressed ErbB proteins allowed analysis of the covalently held complexes. Expression of ErbB-4 alone conferred to CHO cells the ability to form complexes with NRG-4, as well as with NRG-1 (FIG. 4b). In line with the lower mitogenic activity of NRG-4, the covalent crosslinking signal obtained with this ligand was weaker than that observed with a radioactive NRG-1. Nevertheless, both monomers and dimers of ErbB-4 were formed by the two ligands (detection of NRG-4-containing dimers required longer film exposures). Co-expression of ErbB-1 or ErbB-3 did not significantly affect the radioactive signals, but in the case of ErbB-2 an enhancement effect was observed with NRG-1.

The ability of anti-ErbB-1 and anti-ErbB-2 antibodies to precipitate NRG-4-labeled monomeric and dimeric receptor species (FIG. 4B) is probably due to co-immunoprecipitation of ErbB-4 and it indicates the existence of NRG-4-promoted heterodimers with ErbB-1 and ErbB-2. Interestingly, ErbB-3 largely escaped heterodimerization with ErbB-4 following binding of NRG-1 or NRG-4.

Taken together, the biological effects of NRG-4 and its complex formation with ErbB-4 implied not only specificity of recognition, but also weaker interaction relative to NRG-1. To quantify the interaction, a ligand displacement analysis on ErbB-4-expressing CHO cells was undertaken. The ability of unlabeled NRG-4 to displace surface-bound radiolabeled NRG-1β was compared with that of unlabeled NRG-1. The results of this experiment indicated an approximately 8-fold lower binding affinity of NRG-4 to ErbB-4 (FIG. 4c). While NRG-1 bound with an apparent affinity that lies in the low nM range, NRG-4 displayed an apparent approximate kDa of 20 nM. In conclusion, NRG-4 specifically binds to ErbB-4 with an affinity is lower than that of NRG-1β. Because it was previously reported that relative to NRG-1β the alpha isoform displays a 5 to 8-fold lower affinity to both ErbB-3 and ErbB-4 (Tzahar et al., 1994), it is conceivable that NRG-4 and NRG-1α bind to ErbB-4 with similar affinities.

Evidently, NRG-4 binds to ErbB-4 and mediates cell proliferation through activation of this receptor. Because other ErbB ligands stimulate cell growth via tyrosine phosphorylation of their respective receptors and activation of the intervening mitogen-activated protein kinase (MAPK) cascade, these two signaling steps were tested in NRG-4-responsive myeloid cells expressing ErbB-4 (D4 and D24 cell lines). Cells were stimulated with 100 ng/ml of activating ligand for five minutes, followed by lysis and analysis by immunoblotting. NRG-4 stimulated phosphorylation of the 180-kDA ErbB receptors in D4 and in D24 cells with an accompanying activation of MAP-kinase (Erk-1 and Erk-2) also detected (FIG. 5). In contrast to these two cell lines, and consistent with the growth and binding assays, NRG-4 at doses as high as 1 μg/ml, did not stimulate the other 32D cell lines (D1, D2, D3, D12, D13, and D23 cells).

These results further support the conclusion that NRG-4 is a bona fide ligand of the ErbB receptor family that selectively interacts with receptor complexes containing ErbB-4.

Figure 6:
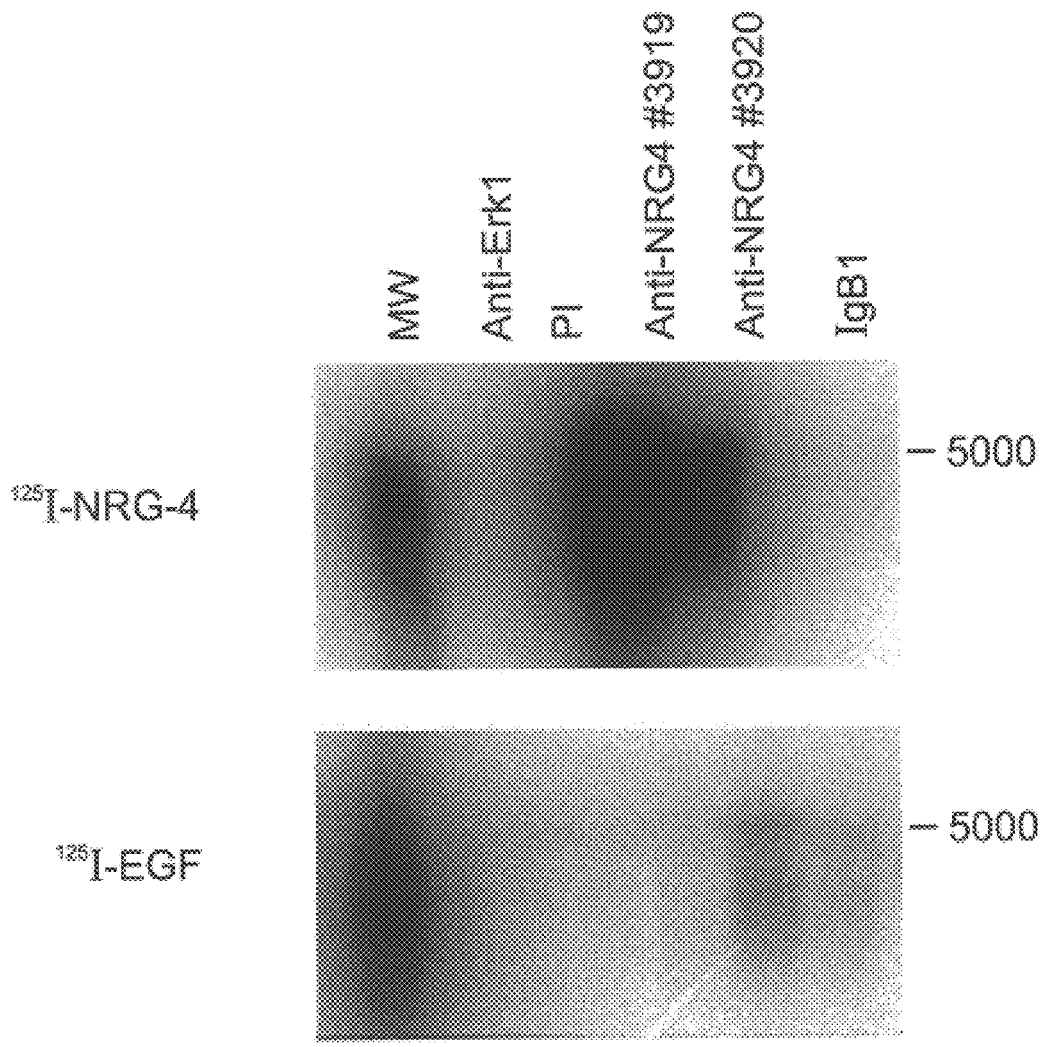
FIG. 6 shows that antibodies generated against the refolded EGF-like domain of NRG-4 Neutralize ligand function. Synthetic refolded NRG-4 peptide was injected into two rabbits by standard adjuvant protocol. After four repeat injections, antisera were collected and tested for specificity by its binding to radiolabeled NRG-4. For non-specific ligand control, radiolabeled EGF was also tested for binding. Hot ligand was separately incubated with sera generated from the two rabbits, along with for controls, pre-immune serum from the first rabbit (#3919), serum generated against a non-relevant epitope (anti-Erk-1) and IgB1 to act as a positive control to demonstrate $^{125}$I-EGF activity. These results demonstrate that the two anti-sera are extremely potent and specific blockers of the NRG-4 EGF-like domain. These antibodies therefore will compete with NRG-4 ligand binding to ErbB receptors.

Neutralizing antibodies to block NRG-4:

Neutralizing antibodies against the EGF-domain of NRG-4 were prepared. Such antibodies are particularly useful as they can block NRG-4 binding to its target receptor and can therefore be utilized in a pharmaceutical context. Synthetic refolded NRG-4 peptide was injected into two rabbits by standard adjuvant protocol. After four repeat injections, antisera were collected and tested for specificity by its binding to radiolabeled NRG-4. For ligand control, radiolabeled EGF was also tested for binding. Hot ligand was separately incubated with sera generated from the two rabbits, along with for controls, pre-immune serum from one of these rabbits, serum generated against a non-relevant epitope (anti-Erk-1) and IgB1 to act as a positive control to demonstrate 125-I EGF activity (FIG. 6). These results demonstrate that the two anti-sera are extremely potent and specific blockers of the NRG-4 EGF-like domain. These antibodies therefore will compete with NRG-4 ligand binding to ErbB receptors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Alimandi M, Wang L-M, Bottaro D, Lee C-C, Angera K, Frankel M, Fedi P, Tang F, Tang C, Lippman M and Pierce J H. (1997). *EMBO J.*, 16, 5608–5617.
2. Barbacci E G, Guarino B C, Stroh J G, Singleton D H, Rosnack K J, Moyer J D and Andrews G C. (1995). *J. Biol. Chem.*, 270, 9585–9589.
3. Ben-Baruch, N. & Yarden, Y. (1994). *Proc. Soc. Exp. Biol. & Med*, 206, 221–7.
4. Ben-Baruch N, Alroy I and Yarden Y. (1998) *Hormones and growth factors in development and neoplasia*. Dickson R B and Salomon D S (eds). Kulwer Academic Publishers: Boston, pp. 145–168.
5. Burden S and Yarden Y. (1997). *Neuron*, 18, 847–855.
6. Busfield S M, Michnick D A, Chickering T W, Revett T L, Ma J, Woolf E A, Comrack R A, Dussault G J, Woolf J, Goodearl A D J and Gearing D P. (1997). *Mol. Cell Biol.*, 17, 4007–4014.
7. Carpenter G and Cohen S. (1979). *Ann. Rev. Biochem.*, 48, 193–216.
8. Carraway K L, Weber J L, Unger M J, Ledesma J, Yu N and Gassmann M. (1997). *Nature*, 387, 512–516.
9. Chan S D, Antoniucci D M, Fok K S, Alajoki M L, Harkins R N, Thompson S A and Wada H G. (1995). *J Biol Chem*, 270, 22608–13.
10. Chang H, Riese D, Gilbert W, Stern D F and McMahan U J. (1997). *Nature*, 387, 509–512.
11. Chen X, Levkowitz G, Tzahar E, Karunagaran D, Lavi S, Ben-Baruch N, Leitner O, Ratzkin B J, Bacus S S and Yarden Y. (1996). *J. Biol. Chem.*, 271, 7620–7629.
12. Cohen B D, Kiener P K, Green J M, Foy L, Fell H P and Zhang K. (1996). *J. Biol. Chem.*, 271, 30897–30903.
13. Elenius K, Paul S, Allison G, Sun J and Klagsbrun M. (1997). *EMBO J.*, 16, 1268–1278.
14. Erickson S L, O'Shea K S, Ghaboosi N, Loverro L, Frantz G, Bauer M, Lu L H and Moore M W. (1997). *Development*, 124, 4999–5011.
15. Gassmann M, Casagranda F, Orioli D, Simon H, Lai C, Klein R and Lemke G. (1995). *Nature*, 378, 390–394.
16. Graus-Porta D, Beerli, R. R. and Hynes N E. (1995). *Mol. Cell Biol.*, 15, 1182–1191.
17. Gregory H, Walsh S and Hopkins C R. (1979). *Gastroenterlogy*, 77.
18. Guy P M, Platko J V, Cantley L C, Cerione R A and Carraway K L. (1994). *Proc. Natl. Acad. Sci. USA*, 91, 8132–8136.
19. Higashiyama S, Abraham J A, Miller J, Fiddes J C and Klagsbrun M. (1991). *Science*, 251, 936–939.

20. Higashiyama S, Horikawa M, Yamada K, Ichino N, Nakano N, Nakagawa T, Miyagawa J, Matsushita N, Nagatsu T, Taniguchi N and Ishiguro H. (1997). *J. Biochem.*, 122, 675–80.
21. Holmes W E, Sliwkowski M X, Akita R W, Henzel W J, Lee J, Park J W, Yansura D, Abadi N, Raab H, Lewis G D, Shepard M, Wood W I, Goeddel D V and Vandlen R L. (1992). *Science*, 256, 1205–1210.
22. Jones J T, Ballinger M D, Pisacane P I, Lofgren J A, Fitzpatrick V D, Fairbrother W J, Wells J A and Sliwkowski M X. (1998). *J Biol Chem*, 273, 11667–11674.
23. Karunagaran D, Tzahar E, Beerli R R, Chen X, Graus-Porta D, Ratzkin B J, Seger R, Hynes N E and Yarden Y. (1996). *EMBO J.*, 15, 254–264.
24. Karunagaran D, Tzahar E, Liu N, Wen D and Yarden Y. (1995). *J. Biol. Chem.*, 270, 9982–9990.
25. Klapper L N, Vaisman N, Hurwitz E, Pinkas-Kramarski R, Yarden Y and Sela M. (1997). *Oncogene*, 14, 2099–2109.
26. Klapper, L. N., Kirschbaum, M. H., Sela, M. & Yarden, Y. (2000). *Adv Cancer Res*, 77, 25–79.
27. Kyte J and Doolittle R F. (1982). *J. Mol. Biol.*, 157, 105–132.
28. Lee K F, Simon H, Chen H, Bates B, Hung M C and Hauser C. (1995). *Nature*, 378, 394–398.
29. Lin X-Z, Capooraco G, Chang P-Y, Ke X-H and Tam J P. (1988). *Biochemistry*, 27, 5640–5645.
30. Marchionni M A, Goodearl A D J, Chen M S, Bermingham-McDonogh O, Kirk C, Hendricks M, Denehy F, Misumi D, Sudhalter J, Kobayashi K, Wroblewski D, Lynch C, Baldassare M, Hiles I, Davis J B, Hsuan J J, Totty N F, Otsu M, McBury R N, Waterfield M D, Stroobant P and Gwynne D. (1993). *Nature*, 362, 312–318.
31. Marquardt H, Hunkapiller M H, Hood L E and Todaro G J. (1984). *Science*, 223, 1079–1082.
32. Massague J and Pandiella A. (1993). *Ann. Rev. Biochem.*, 62, 515–541.
33. Meyer D and Birchmeier C. (1995). *Nature*, 378, 386–390.
34. Mosman T. (1983). *J. Immunol. Methods*, 65, 55–63.
35. Peles E, Bacus S S, Koski R A, Lu H S, Wen D, Ogden S G, Ben-Levy R and Yarden Y. (1992). *Cell*, 69, 205–216.
36. Peles E, Ben-Levy R, Tzahar E, Liu N, Wen D and Yarden Y. (1993). *EMBO J.*, 12, 961–971.
37. Pinkas-Kramarski R, Eilam R, Alroy I, Levkowitz G, Lonai P and Yarden Y. (1997). *Oncogene*, 15, 2803–2815.
38. Pinkas-Kramarski R, Guarino B C, Shelly M, Wang L M, Lyass L, Alroy I, Alimandi M, Kuo A, Moyer J D, Lavi S, Eisenstein M, Ratzkin B J, Seger R, Bacus S S, Pierce J H, Andrews G C and Yarden Y. (1998). *Mol. Cell Biol.*, 18, 6090–6101.
39. Pinkas-Kramarski R, Soussan L, Waterman H, Levkowitz G, Alroy I, Klapper L, Lavi S, Seger R, Ratzkin B, Sela M and Yarden Y. (1996). *EMBO J.*, 15, 2452–2467.
40. Plowman G D, Culouscou J M, Whitney G S, Green J M, Carlton G W, Foy L, Neubauer M G and Shoyab M. (1993). *Proc. Natl. Acad. Sci. U S A*, 90, 1746–1750.
41. Reddy C C, Niyogi S K, Wells A, Wiley H S and Lauffenburger D A. (1996). *Nature Biotech.*, 14, 1696–1699.
42. Riese D J, Bermingham Y, van Raaij T M, Buckley S, Plowman G D and Stern D F. (1996a). *Oncogene*, 12, 345–353.
43. Riese D J, Kim E D, Elenius K, Buckley S, Klagsbrun M, Plowman G D and Stern D F. (1996b). *J. Biol. Chem.*, 271, 20047–20052.
44. Riese D J, van Raaij T M, Plowman G D, Andrews G C and Stern D F. (1995). *Mol. Cell Biol.*, 15, 5770–5776.
45. Riethmacher D, Sonnenberg R E, Brinkmann V, Yamaai T, Lewin G R and Birchmeier C. (1997). *Nature*, 389, 725–30.
46. Samuel K and Altschul S F. (1990). *Proc. Natl. Acad. Sci. USA*, 87, 2264–68.
47. Shelly M, Pinkas-Kramarski R, Guarino B C, Waterman H, Wang L-M, Lyass L, Alimandi M, Kuo A, Bacus S S, Pierce J H, Andrews G C and Yarden Y. (1998). *J. Biol. Chem.*, 273, 10496–10505.
48. Shing Y, Christofori G, Hanahan D, Ono Y, Sasada R, Igarashi K. and Folkman J. (1993). *Science*, 259, 1604–7.
49. Shoyab M, Plowman G D, McDonald V L, Bradley J B and Todaro G J. (1989). *Science*, 243, 1074–1076.
50. Sliwkowski M X, Schaefer G, Akita R W, Lofgren J A, Fitzpatrick V D, Nuijens A, Fendly B M, Cerione R A, Vandlen R L and Carraway K L. (1994). *J. Biol. Chem.*, 269, 14661–14665.
51. Smith T F and Waterman M S. (1981). *Adv. Appl. Math.*, 2, 482–89.
52. Tam J P, Heath W F and Merrifield R B. (1983). *J. Am. Chem. Soc.*, 105, 6442–6445.
53. Toyoda H, Komursaki T, Uchida D, Takayama Y, Isobe T, Okuyama T and Hanada K. (1995). *J. Biol. Chem.*, 270, 7495–7500.
54. Tzahar E, Levkowitz G, Karunagaran D, Yi L, Peles E, Lavi S, Chang D, Liu N, Yayon A, Wen D and Yarden Y. (1994). *J. Biol. Chem.*, 269, 25226–25233.
55. Tzahar E, Pinkas-Kramarski R, Moyer J, Klapper L N, Alroy I, Levkowitz G, Shelly M, Henis S, Eisenstein M, Ratzkin B J, Sela M, Andrews G C and Yarden Y. (1997). *EMBO J.*, 16, 4938–4950.
56. Tzahar E, Waterman H, Chen X, Levkowitz G, Karunagaran D, Lavi S, Ratzkin B J and Yarden Y. (1996). *Mol. Cell Biol.*, 16, 5276≧5287.
57. Tzahar E and Yarden Y. (1998). *BBA Rev. Cancer*, 1377, M25–M37.
58. Wang L M, Kuo A, Alimandi M, Veri M C, Lee C C, Kapoor V, Ellmore N, Chen X H and Pierce J H. (1998). *Proc. Natl. Acad. Sci. USA*, 95, 6809–6814.
59. Wen D, Peles E, Cupples R, Suggs S V, Bacus S S, Luo Y, Trail G, Hu S, Silbiger S M, Ben-Levy R, Luo Y and Yarden Y. (1992). *Cell*, 69, 559–572.
60. Wen D, Suggs S V, Karunagaran D, Liu N, Cupples R L, Luo Y, Jansen A M, Ben-Baruch N, Trollinger D B, Jacobson V L, Meng T, Lu H S, Hu S, Chang D, Yanigahara D, Koski R A and Yarden Y. (1994). *Mol. Cell Biol.*, 14, 1909–1919.
61. Yung Y, Dolginov Y, Yao Z, Rubinfeld H, Michael D, Hanoch T, Roubini E, Lando Z, Zharhari D and Seger R. (1997). *FEBS J.*, 408, 292–296.
62. Zhang D, Sliwkowski M X, Mark M, Frantz G, Akita R, Sun Y, Hillan K, Crowley C, Brush J and Godowski P J. (1997). *Proc. Natl. Acad. Sci. USA*, 94, 9562–9567.

What is claimed is:

1. An isolated nucleic acid comprising a polynucleotide sequence encoding a polypeptide being capable of binding to a mammalian ErbB-4 receptor and including an amino acid sequence being at least 95% homologous to an EGF-like domain of SEQ ID NO:15, as determined using the BestFit software of the Wisconsin sequence analysis package, utilizing the Smith and Waterman algorithm, where gap creation penalty equal 8 and gap extension penalty equals 2.

2. The isolated nucleic acid of claim 1, wherein said polypeptide includes the amino acid sequence defined by amino acid coordinates 4–50 of SEQ ID NO:15.

3. The isolated nucleic acid of claim 1, wherein said polypeptide includes the amino acid sequence defined by amino acid coordinates 1–90 of SEQ ID NO:15.

4. The isolated nucleic acid of claim 1, wherein said EGF-like domain is encoded by the nucleic acid sequence set forth in SEQ ID NO:14.

5. The isolated nucleic acid of claim 1, having a nucleic acid sequence at least 80% identical to a nucleic acid sequence set forth in SEQ ID NO:14, as determined using the BestFit software of the Wisconsin sequence analysis package, utilizing the Smith and Waterman algorithm, where gap weight equals 50, length weight equals 3, average match equals 10 and average mismatch equals −9.

6. A nucleic acid construct comprising the isolated nucleic acid of claim 1.

7. The nucleic acid construct of claim 6, further comprising a promoter for regulating expression of the isolated nucleic acid in an orientation selected from the group consisting of sense and antisense orientation.

8. A host cell comprising the nucleic acid construct of claim 6.

* * * * *